United States Patent [19]
Lociuro et al.

[11] Patent Number: 5,891,869
[45] Date of Patent: Apr. 6, 1999

[54] BASIC OXAZOLINE-AMIDE DERIVATIVES OF GE2270 AND GE2270-LIKE ANTIBIOTICS

[75] Inventors: Sergio Lociuro, Verona; Pierfausto Seneci, Desenzano del Garda; Romeo Ciabatti, Novate Milanese, all of Italy

[73] Assignee: Biosearch Italia, S.p.A., Italy

[21] Appl. No.: 875,715

[22] PCT Filed: Feb. 1, 1996

[86] PCT No.: PCT/EP96/00425

§ 371 Date: Jul. 31, 1997

§ 102(e) Date: Jul. 31, 1997

[87] PCT Pub. No.: WO96/24608

PCT Pub. Date: Aug. 15, 1996

[30] Foreign Application Priority Data

Feb. 7, 1995 [EP] European Pat. Off. ............. 95101596

[51] Int. Cl.$^6$ ................ C07K 5/06; C07K 7/56; A61K 38/05
[52] U.S. Cl. ............................. 514/183; 540/451
[58] Field of Search ............... 514/183; 540/451

[56] References Cited

U.S. PATENT DOCUMENTS

| | | | |
|---|---|---|---|
| 5,139,778 | 8/1992 | Selva et al. | 424/117 |
| 5,202,241 | 4/1993 | Selva et al. | 435/91.3 |
| 5,514,649 | 5/1996 | Selva et al. | 514/9 |
| 5,599,791 | 2/1997 | Tavecchia et al. | 540/451 |

FOREIGN PATENT DOCUMENTS

| | | |
|---|---|---|
| 451 486 | 10/1991 | European Pat. Off. . |
| 0 494 078 | 7/1992 | European Pat. Off. . |
| 529410 | 3/1993 | European Pat. Off. . |
| WO 92/12172 | 7/1992 | WIPO . |
| WO 96/24607 | 8/1996 | WIPO . |
| WO 97/30078 | 8/1997 | WIPO . |

OTHER PUBLICATIONS

Shimanaica "Novel Antibiotics, Amythiamicins III. Structure Elucidations of Amythiamicins A, B and C" The Journal of Antibiotics, vol. 47 No. 10, pp. 1153–1159, (1994).

*Primary Examiner*—Donald G. Daus
*Attorney, Agent, or Firm*—Killworth, Gottman, Hagan & Schaeff, L.L.P.

[57] ABSTRACT

The present invention refers to basic oxazoline-amide derivatives of GE 2270 and GE 2270-like antibiotics of general formula (I), wherein the group GE represents the antibiotic core molecule. The amide derivatives of antibiotic GE 2270 of formula (I) are antimicrobial agents mainly active against gram positive bacteria.

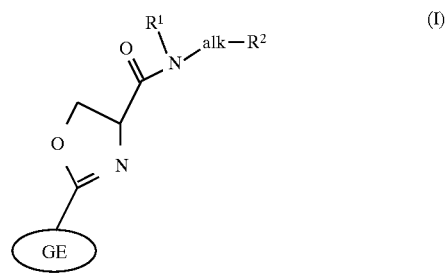

47 Claims, No Drawings

BASIC OXAZOLINE-AMIDE DERIVATIVES OF GE2270 AND GE2270-LIKE ANTIBIOTICS

The present invention refers to basic amide derivatives of GE2270 and GE2270-like antibiotics of general formula I

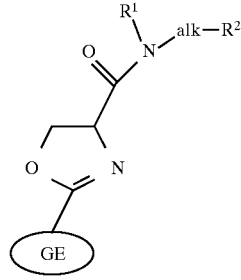

wherein:

$R^1$ represents hydrogen, $(C_1-C_4)$alkyl or di$(C_1-C_4)$alkylamino$(C_1-C_4)$alkylene;

alk represents $(C_1-C_4)$alkylene, $(C_2-C_5)$alkylene-carbonyl or a five or six membered nitrogen containing heterocycle ring;

$R^2$ represents aminocarbonyl, mono or di$(C_1-C_4)$alkyl-aminocarbonyl, or a $NR^3R^4$ group wherein $R^3$ represents $(C_1-C_4)$alkyl, hydroxy$(C_1-C_4)$alkylene, or di$(C_1-C_4)$alkylamino-$(C_1-C_4)$alkylene, and $R^4$ represents $(C_1-C_4)$alkyl, di$(C_1-C_4)$alkylamino-$(C_1-C_4)$alkylene or hydroxy$(C_1-C_4)$alkylene, or a five or six membered heterocycle ring containing one nitrogen atom and optionally a further heteroatom selected from nitrogen and oxygen, optionally substituted with a group selected from $(C_1-C_4)$alkyl, hydroxy$(C_1-C_4)$alkylene, di$(C_1-C_4)$alkylamino or di$(C_1-C_4)$alkylamino$(C_1-C_4)$alkylene;

or $R^1$ and alk-$R^2$ together with the adjacent nitrogen atom form a five or six membered heterocycle ring optionally containing a further heteroatom selected from oxygen and nitrogen, optionally substituted with a group selected from $(C_1-C_4)$alkyl, di$(C_1-C_4)$alkylamino, di$(C_1-C_4)$ alkylamino $(C_1-C_4)$alkylene, hydroxy$(C_1-C_4)$alkylene and a alk$_2$-$R^5$ group wherein alk$_2$ is $(C_1-C_4)$alkyl and $R^5$ is a $NR^6R^7$ group wherein $R^6$ represents $(C_1-C_4)$alkyl or di$(C_1-C_4)$alkylamino $(C_1-C_4)$alkylene and $R^7$ represents $(C_1-C_4)$alkyl or di$(C_1-C_4)$alkylamino $(C_1-C_4)$alkylene or a five or six membered heterocycle ring containing one or two heteroatoms selected from nitrogen and oxygen, optionally substituted with a group selected from $(C_1-C_4)$alkyl, hydroxy$(C_1-C_4)$alkylene, di$(C_1-C_4)$alkylamino and di$(C_1-C_4)$alkylamino $(C_1-C_4)$alkylene.

and the group of formula

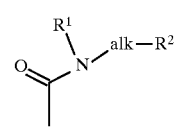

represents the antibiotic core portion of formula

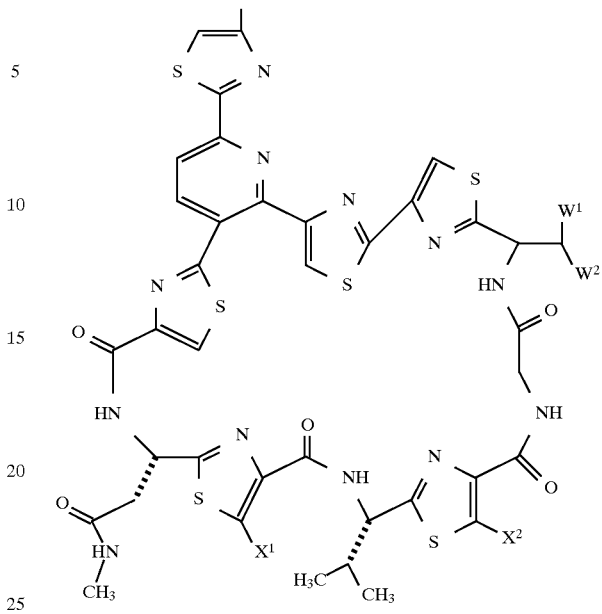

wherein:

$W^1$ represents phenyl $W^2$ represents hydroxy or both $W^1$ and $W^2$ represent methyl, $X^1$ represents hydrogen or methyl, $X^2$ represents hydrogen, methyl or methoxymethylen, with the proviso that when both $W^1$ and $W^2$ are methyl, then $X^1$ is methyl and $X^2$ is hydrogen, or a pharmaceutical acceptable salt thereof.

The present invention refers also to the processes for preparing the compounds of formula I and to the carboxylic acid and protected carboxylic acid derivatives of the above compounds, i.e. the precursors of the compounds of formula I wherein the amidic group:

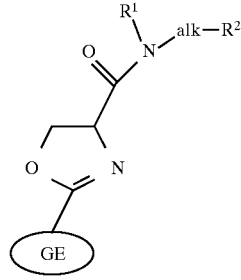

is substituted by the group —COOY, wherein Y represents hydrogen or $(C_1-C_4)$alkyl.

Antibiotic GE 2270 is prepared by culturing a sample of *Planobispora rosea* ATCC 53773 or a producing variant or mutant thereof and isolating the desired antibiotic substance from the mycelium and/or the fermentation broth. *Planobispora rosea* ATCC 53773 was isolated from a soil sample and deposited on Jun. 14, 1988 with the American Type Culture Collection (ATCC), 12301 Parklawn Drive, Rockville, Md. 20852 Maryland, U.S.A., under the provisions of the Budapest Treaty. The strain has been accorded accession number ATCC 53773.

Antibiotic GE 2270 factor A is the main component of the antibiotic GE 2270 complex. Antibiotic GE 2270 factor A and *Planobispora rosea* ATCC 53773 are described in U.S. Pat. No. 5,139,778.

At present, a number of minor factors of antibiotic GE 2270 have been isolated, namely factors $B_1$, $B_2$, $C_1$, $C_2$, $D_1$, $D_2$, E and T disclosed in European Patent Application Publication no. 451486 which has as its equivalent, U.S. Pat.

No. 5,747,295 and factor $C_{2a}$ is disclosed in European Patent Application Publication no. 529410 which has as its equivalent, U.S. Pat. No. 5,514,649. Also degradation products of GE 2270 factor A are known, namely factors $A_1$, $A_2$, $A_3$ and H disclosed in U.S. Pat. No. 5,139,778.

Among these compounds, factor A, $B_2$, $C_1$ and $C_2$ may be employed as suitable starting materials for preparing the compounds of the present invention.

The above factors may be represented by the following formula II:

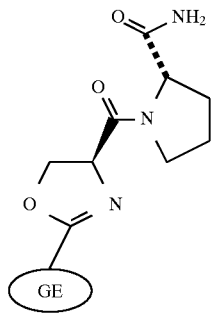

II wherein

is a group as above defined wherein
$W^1$ is phenyl and $W^2$ is hydroxy and
when $X^1$ is $CH_3$ and $X^2$ is $CH_2OCH_3$, factor A is determined;
when $X_1$ is $CH_3$ and $X^2$ is $CH_3$, factor $B_2$ is determined;
when $X_1$ is $CH_3$ and $X^2$ is H, factor $C_1$ is determined; and
when $X^1$ is H and $X^2$ is $CH_2OCH_3$, factor $C_2$ is determined.

It should be noted that this formula does not correspond to the one disclosed in the above cited Patent Applications, which formula was assigned on the basis of the physicochemical data reported therein. As a matter of fact, further studies on the degradation products of the GE2270 factors (P. Tavecchia et al., Jour. of Antib., 47, no. 12 (1994), 1564–1567) have lead to the conclusion that the surmised aminoacid sequence was not correct, as the two aminoacids bearing the moieties $X^1$ and $X^2$ were actually in an opposite sequence in comparison with the formula previously reported; therefore the present formula II has been proposed for correctly representing the structure of antibiotic GE 2270.

A GE 2270-like antibiotic of formula IIa:

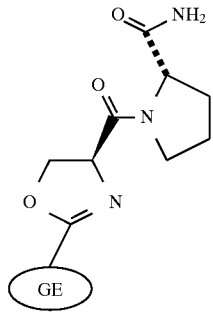

IIa wherein GE is a group as above defined wherein
both $W^1$ and $W^2$ are methyl, $X^1$ is methyl and $X^2$ is hydrogen,
has been described by K. Shimanaka et al., Journal of Antibiotics, vol.47, pp. 668–674 (isolation, physicochemical characteristics, antimicrobial activity) and vol. 47, pp. 1153–1159 (structure elucidation); both these articles are herein incorporated by reference.

Said GE 2270-like antibiotic, named amythiamicin factor A, has been isolated from the fermentation broth of Amycolatopsis sp. MI481-42F4, which strain has been deposited in the National Institute of Bioscience and Human-Technology, Agency of Industrial Science and Technology, Japan, with the accession No. FERM P-12739.

The fermentation of Amycolatopsis sp. MI481-42F4 is conducted according to conventional methodologies in conventional nutrient medium; amythiamicin factor A shows antimicrobial activity against gram positive bacteria. Also this compound may suitably be employed as starting material for the process of the present invention.

In the following of the present specification, with the wording "GE 2270 starting material" is intended any suitable factor of antibiotic GE 2270, such as factor A, $B_2$, $C_1$ and $C_2$, as well as amythiamicin factor A.

Furthermore, amide derivatives of GE 2270 derivatives of general formula

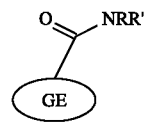

wherein the group GE is as defined in formula II and R and R' have a plurality of meanings, are described in European Patent Application Publication No. 565567 which has its equivalent, U.S. Pat. No. 5,599,791 (also in this case, for the reasons set forth before, the disclosed structure of the core portion is uncorrect).

As evident, the above amide derivatives of GE 2270 differ from the compounds of the present invention in that the compounds of the invention contain an oxazoline ring between the core portion GE and the amidic moiety.

In the present description, the terms used above in defining the meanings of the substituents are intended to have the meanings commonly assigned to them in the art. Accordingly:

($C_1$–$C_4$)alkyl represents a linear or branched hydrocarbon moiety containing 1, 2, 3 or 4 carbon atoms such as:
—$CH_3$,
—$CH_2$—$CH_3$,
—$CH_2$—$CH_2$—$CH_3$,
—CH—($CH_3$)$_2$,
—$CH_2$—$CH_2$—$CH_2$—$CH_3$,
—CH($CH_3$)—$CH_2$—$CH_3$,
—$CH_2$—CH($CH_3$)—$CH_3$,
—C—($CH_3$)$_3$;

($C_1$–$C_4$)alkylene represents a bifunctional linear or branched hydrocarbon moiety containing 1, 2, 3 or 4 carbon atoms such as:
—$CH_2$—,
—$CH_2$—$CH_2$—,
—CH($CH_3$)—
—$CH_2$—$CH_2$—$CH_2$—,
—CH($CH_3$)—$CH_2$—,
—$CH_2$—$CH_2$—$CH_2$—$CH_2$—,
—CH($CH_3$)—$CH_2$—$CH_2$—,
—$CH_2$—CH($CH_3$)—$CH_2$—
—C($CH_3$)$_2$—$CH_2$—;

($C_1$–$C_4$)alkylenecarbonyl represents a bifunctional carbonylic moiety containing 2 to 5 carbon atoms, such as:
—$CH_2$—CO—,
—$CH_2$—$CH_2$—CO—,
—CH($CH_3$)—CO—,
—$CH_2$—$CH_2$—$CH_2$—CO—,
—CH($C_2H_5$)—CO—,
—CH($CH_3$)—$CH_2$—CO—,
—CH($C_2H_5$)—$CH_2$—CO—,
—$CH_2$—$CH_2$—$CH_2$—$CH_2$—CO—,
—CH($CH_3$)—$CH_2$—$CH_2$—CO—,
—C($CH_3$)$_2$—$CH_2$—CO—;

hydroxy($C_1$–$C_4$)alkylene represents a linear or branched alcanolic moiety of from 1 to 4 carbon atom, such as:
—$CH_2$—OH,
—$CH_2$—$CH_2$—OH,
—CH($CH_3$)—OH
—$CH_2$—$CH_2$—$CH_2$—OH,
—CH($CH_3$)—$CH_2$—OH,
—$CH_2$—CH($CH_3$)—OH
—$CH_2$—$CH_2$—$CH_2$—$CH_2$—OH,
—CH($CH_3$)—$CH_2$—$CH_2$—OH,
—$CH_2$—CH($CH_3$)—$CH_2$—OH,
—$CH_2$—$CH_2$—CH($CH_3$)—OH
—C($CH_3$)$_2$—$CH_2$—OH;

di($C_1$–$C_4$)alkylamino, is an amino moiety substituted with two linear or branched alkyl groups containing 1, 2, 3 or 4 carbon atoms such as:
—N—($CH_3$)$_2$,
—N($CH_3$)($CH_2$—$CH_3$),
—N($CH_2$—$CH_3$)$_2$,
—N($CH_3$)($CH_2$—$CH_2$—$CH_3$),
—N($CH_2$—$CH_3$)($CH_2$—$CH_2$—$CH_3$),
—N($CH_2$—$CH_2$—$CH_3$)$_2$,
—N($CH_3$)[CH—($CH_3$)$_2$],
—N($CH_2$—$CH_3$)[CH—($CH_3$)$_2$],
—N($CH_3$)($CH_2$—$CH_2$—$CH_2$—$CH_3$),
—N($CH_2$—$CH_3$)($CH_2$—$CH_2$—$CH_2$—$CH_3$),
—N($CH_2$—$CH_2$—$CH_3$)($CH_2$—$CH_2$—$CH_2$—$CH_3$),
—N($CH_2$—$CH_2$—$CH_2$—$CH_3$)$_2$,
—N($CH_2$—$CH_2$—$CH_2$—$CH_3$)[CH—($CH_3$)$_2$];

a five or six membered heterocycle ring according to the meanings of $R^2$ or $R^5$ is an heterocycle ring such as:

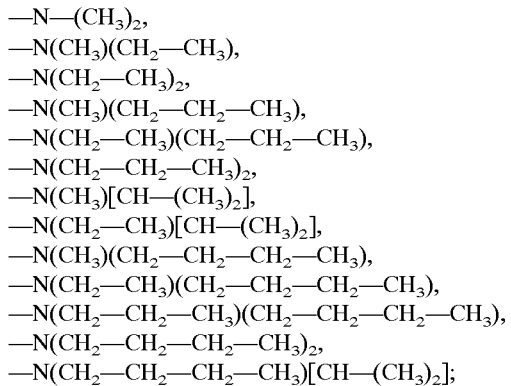
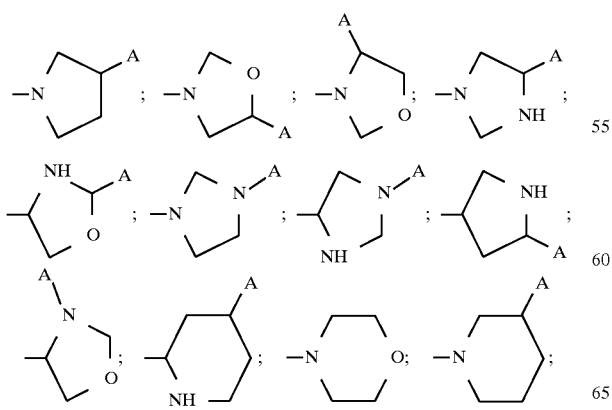
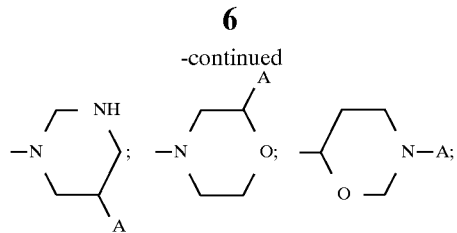
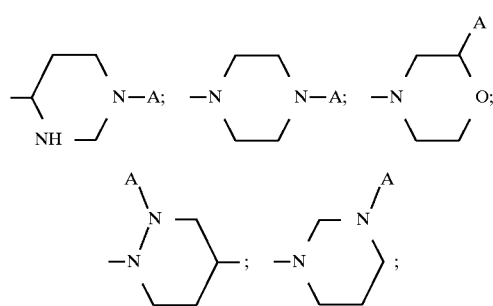

wherein A represents hydrogen or hydroxy($C_1$–$C_4$)alkylene when referring to the substituent "$R^2$" or A represents only hydrogen when referring to the substituent "$R^5$";

a five or six membered heterocycle ring formed by the moieties $R^1$ and alk-$R^2$ together, is an heterocycle ring such as:

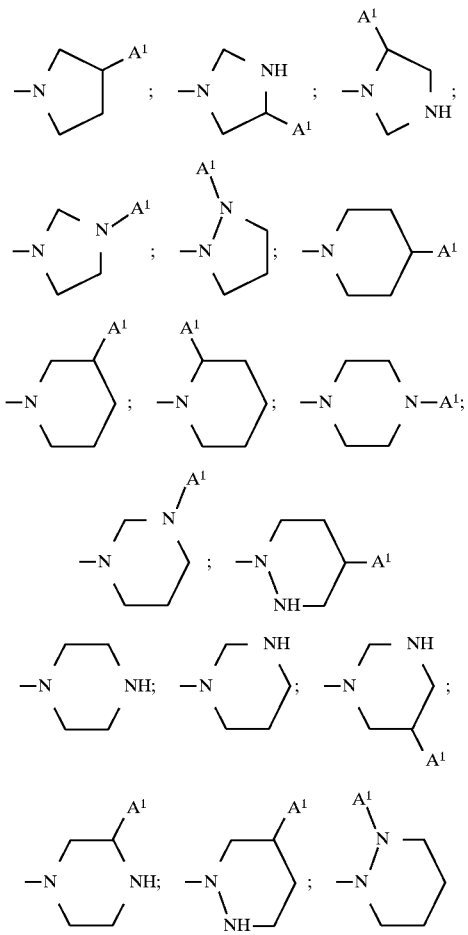

wherein $A^1$ represents hydrogen or the optional substituents of the heterocycle ring as set forth before.

By comparing the above formulas I and II, it appears that GE 2270 factors naturally occur with a determined chirality of the molecule; according to the present invention, the compounds of formula I may be obtained with both the chiralities, with respect to the bond between the oxazoline and the proline rings. Although in most cases, the antimicrobial activity of the two epimers (either of the starting materials or of the compounds of the invention) is almost the same, in some cases, against particular strains (e.g. streptococci), it has been observed a slightly higher antimicrobial activity for those compounds having the chirality corresponding to the natural one.

Thus, a group of preferred compounds of the invention are those compounds of general formula Ia $$\text{Ia}$$

wherein the group GE, $R^1$, alk and $R^2$ are as defined in formula I.

Another group of preferred compounds are those compounds of formula I or Ia wherein the group GE is such that $W^1$ is phenyl, $W^2$ is hydroxy, $X^1$ is methyl, $X^2$ is methoxymethylen and $R^1$, alk and $R^2$ are as defined in formula I.

A further group of preferred compounds are those compounds of formula I or Ia wherein the group GE is as defined in formula I and $R^1$ represents hydrogen or $(C_1$–$C_4)$alkyl, alk represents $(C_1$–$C_4)$alkylene, $(C_2$–$C_5)$alkylenecarbonyl or a five or six membered nitrogen containing heterocycle ring $R^2$ represents aminocarbonyl or a $NR^3R^4$ group wherein
  $R^3$ represents $(C_1$–$C_4)$alkyl and
  $R^4$ represents $(C_1$–$C_4)$alkyl or di$(C_1$–$C_4)$alkylamino $(C_1$–$C_4)$alkylene,
  or a five or six membered heterocycle ring containing one or two nitrogen atoms, optionally substituted with a group selected from $(C_1$–$C_4)$alkyl and hydroxy$(C_1$–$C_4)$alkylene;

or $R^1$ and alk-$R^2$ together with the adjacent nitrogen atom form a five or six membered heterocycle ring optionally containing a further nitrogen atom, optionally substituted with a group selected from $(C_1$–$C_4)$alkyl, di$(C_1$–$C_4)$ alkylamino, di$(C_1$–$C_4)$alkylamino$(C_1$–$C_4)$alkylene and a alk$_2$-$R^5$ group wherein
  alk$_2$ is $(C_1$–$C_2)$alkyl and
  $R^5$ is a $NR^6R^7$ group wherein
    $R^6$ represents $(C_1$–$C_4)$alkyl and
    $R^7$ represents $(C_1$–$C_4)$alkyl or di$(C_1$–$C_4)$alkylamino $(C_1$–$C_4)$alkylene
    or a five or six membered heterocycle ring containing one or two heteroatoms selected from nitrogen and oxygen.

A further group of preferred compounds are those compounds of formula I or Ia wherein the group GE is as defined in formula I and $R^1$ represents hydrogen or $(C_1$–$C_2)$alkyl, alk represents $(C_1$–$C_3)$alkylene, $(C_2$–$C_3)$alkylenecarbonyl or a five membered nitrogen containing heterocycle ring $R^2$ represents aminocarbonyl or a $NR^3R^4$ group wherein
  $R^3$ represents $(C_1$–$C_3)$alkyl and
  $R^4$ represents $(C_1$–$C_3)$alkyl or di$(C_1$–$C_2)$alkylamino $(C_1$–$C_2)$alkylene,
  or a five or six membered heterocycle ring containing one or two nitrogen atoms, optionally substituted with a group selected from $(C_1$–$C_2)$alkyl and hydroxy$(C_1$–$C_2)$alkylene;

or $R^1$ and alk-$R^2$ together with the adjacent nitrogen atom form a five or six membered heterocycle ring optionally containing a further nitrogen atom, optionally substituted with a group selected from $(C_1$–$C_2)$alkyl, di$(C_1$–$C_2)$ alkylamino, di$(C_1$–$C_2)$alkylamino$(C_1$–$C_2)$alkylene and a alk$_2$-$R^5$ group wherein
  alk$_2$ is $(C_1$–$C_2)$alkyl and
  $R^5$ is a $NR^6R^7$ group wherein
    $R^6$ represents $(C_1$–$C_2)$alkyl and
    $R^7$ represents $(C_1$–$C_2)$alkyl or di$(C_1$–$C_2)$alkylamino $(C_1$–$C_2)$alkylene
    or a five or six membered heterocycle ring containing one or two heteroatoms selected from nitrogen and oxygen.

Particularly preferred compounds are those compounds of formula I or Ia wherein the group GE is such that $W^1$ is phenyl, $W^2$ is hydroxy, $X^1$ is methyl, $X^2$ is methoxymethylene and $R^1$ represents hydrogen or $(C_1$–$C_2)$alkyl, alk represents $(C_1$–$C_3)$alkylene, $R^2$ represents a $NR^3R^4$ group wherein
  $R^3$ represents $(C_1$–$C_3)$alkyl and
  $R^4$ represents $(C_1$–$C_3)$alkyl or di$(C_1$–$C_2)$alkylamino $(C_1$–$C_2)$alkylene,
  or a five or six membered heterocycle ring containing one or two nitrogen atoms, optionally substituted with a group selected from $(C_1$–$C_2)$alkyl and hydroxy$(C_1$–$C_2)$alkylene or $R^1$ and alk-$R^2$ together with the adjacent nitrogen atom form a five or six membered heterocycle ring optionally containing a further nitrogen atom, optionally substituted with a group selected from $(C_1$–$C_2)$alkyl, di$(C_1$–$C_2)$ alkylamino, di$(C_1$–$C_2)$alkylamino$(C_1$–$C_2)$alkylene and a alk$_2$-$R^5$ group wherein
  alk$_2$ is $(C_1$–$C_2)$alkylene and
  $R^5$ is a $NR^6R^7$ group wherein
    $R^6$ represents $(C_1$–$C_2)$alkyl and
    $R^7$ represents $(C_1$–$C_2)$alkyl or di$(C_1$–$C_2)$alkylamino $(C_1$–$C_2)$alkylene
    or a five or six membered heterocycle ring containing one or two heteroatoms selected from nitrogen and oxygen.

Examples of —N($R^1$)alk$R^2$ groups, as defined in formula I, are the following:

—NH—$(CH_2)_m$—N$(CH_2)_t(CH_3)$ | $(CH_2)_p CH_3$

—NH—CH—N$(CH_2)_t(CH_3)$ | $(CH_2)_r CH_3$ | $(CH_2)_p CH_3$

—N—$(CH_2)_m$—N$(CH_2)_t(CH_3)$ | $(CH_2)_q CH_3$ | $(CH_2)_p CH_3$

—NH+$(CH_2)_m$—N—CH$(CH_3)$—$(CH_2)_r CH_3$ | CH$(CH_3)$—$(CH_2)_s CH_3$

—N—$(CH_2)_m$—N—CH$(CH_3)$—$(CH_2)_r CH_3$ | $(CH_2)_q CH_3$ | CH$(CH_3)$—$(CH_2)_s CH_3$

—NH—$(CH_2)_m$—CO—N$(CH_2)_t(CH_3)$ | $(CH_2)_p CH_3$

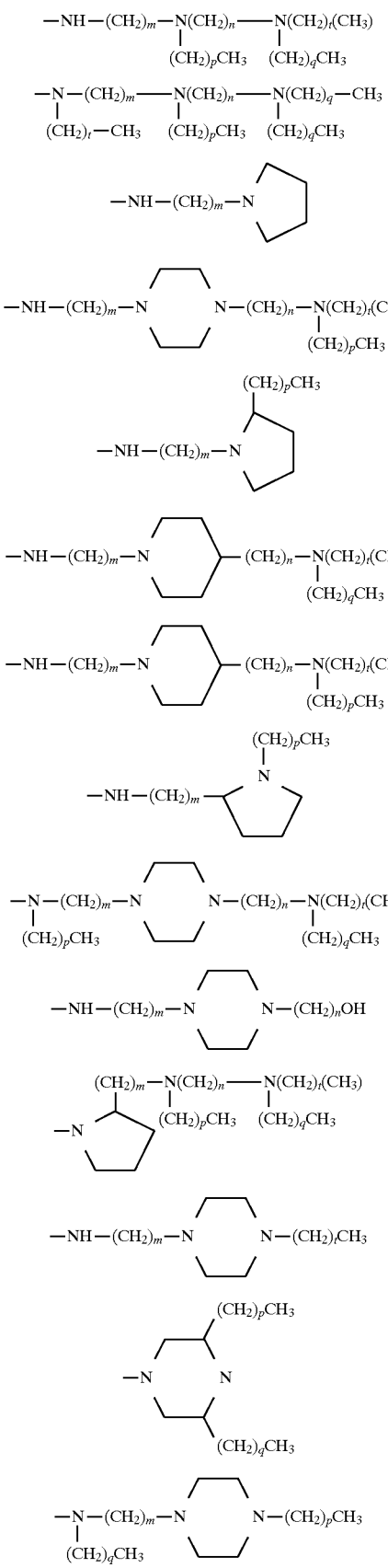
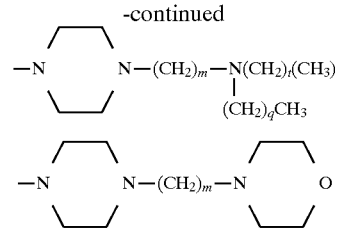
wherein:
m and n=1, 2, 3 or 4;
p, q and t=0, 1, 2 or 3
r and s=0 or 1.
Preferred examples of —N(R¹)alk R² groups are the following:
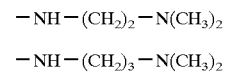
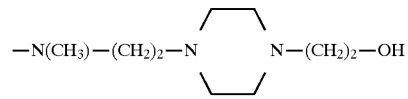
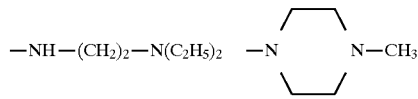
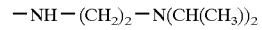
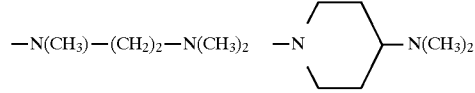
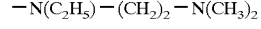
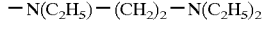
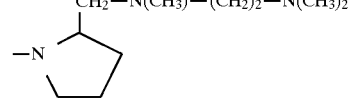
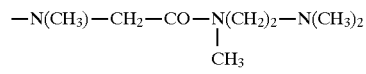
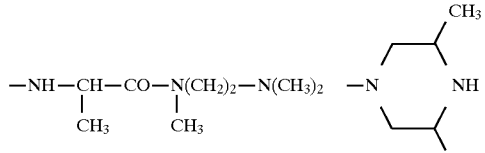
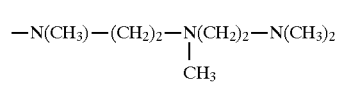
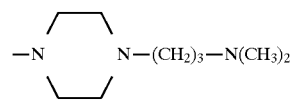
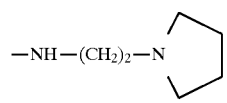

-continued

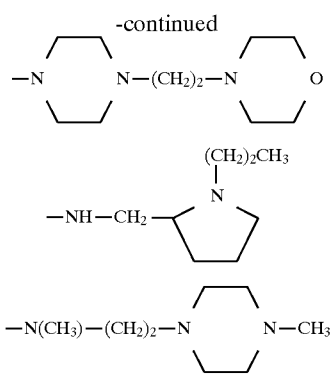

The compounds of the invention can form salts according to conventional procedures.

In particular, those compounds of formula I wherein the group —N(R$^1$)alkR$^2$ contains further amine functions can form acid addition salts.

Preferred addition salts of the compounds of this invention are the pharmaceutically acceptable acid addition salts.

With the term "pharmaceutically acceptable acid addition salts" are intended those salts with acids which from biological, manufacturing and formulation standpoint are compatible with the pharmaceutical practice as well as with the use in the animal growth promotion.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, dodecylsulfonic (estolic), benzenesulfonic, sorbic, picric, benzoic, cinnamic acid and the like.

The transformation of the free amino or non-salt compounds of the invention into the corresponding addition salts, and the reverse, i.e. the transformation of an addition salt of a compound of the invention into the non-salt or free amino form, are within the ordinary technical skill and are encompassed by the present invention. The only precaution is to avoid solutions with pH lower than 4–5 when preparing the addition salt (for avoiding the opening of the oxazolinic ring) and solutions with a pH higher than 8–9 when freing the base (for avoiding epimerization on the chiral center).

For instance, a compound of formula I can be transformed into the corresponding acid addition-salt by dissolving the non-salt form in an aqueous solvent and adding a slight molar excess of the selected acid. The resulting solution or suspension is then lyophilized to recover the desired salt. Instead of lyophilizing, in some instances, it is possible to recover the final salt by extraction with an organic solvent, concentration to a small volume of the separated organic phase and precipitation by adding a non-solvent.

In case the final salt is unsoluble in an organic solvent where the non-salt form is soluble, it may be recovered by filtration from the organic solution of the non-salt form after addition of the stoichiometric amount or a slight molar excess of the selected acid.

The non-salt form can be prepared from a corresponding acid salt dissolved in an aqueous solvent which is then neutralized to free the non-salt form. This is then recovered for instance by extraction with an organic solvent or is transformed into another acid addition salt by adding the selected acid and working up as above.

A common desalting procedure may be employed when, following the neutralization, desalting is necessary.

For example, column chromatography on controlled pore polydextrane resins (such as Sephadex LH 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100% acetonitrile.

As is known in the art, the salt formation either with pharmaceutically acceptable acids or non-pharmaceutically acceptable acids may be used as a convenient purification technique. After formation and isolation, salt form of a compound of formula I can be transformed into the corresponding non-salt or into a pharmaceutically acceptable salt.

In some instances the acid addition salt of a compound of formula I is more soluble in water and hydrophilic solvents and has an increased chemical stability. Good solubility and stability in water or hydrophylic solvents of an active compound are in general appreciated in the art, for the preparation of suitable pharmaceutical compositions for the administration of the medicament.

However, in view of the similarity of the properties of the compounds of formula I and their salts, what is said in the present application when dealing with the biological activities of the compounds of formula I applies also to their pharmaceutically acceptable salts, and viceversa.

A suitable method for preparing the compounds of the invention (hereinafter defined as "Method A") comprises a) reacting a compound of formula III

wherein the group GE is as defined in formula I, with a suitable serinamide of formula IV:

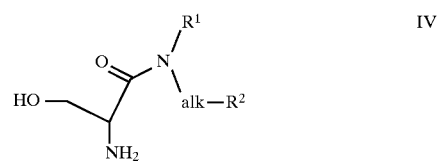

wherein R$^1$, alk and R$^2$ are as in formula I, in an inert aprotic organic solvent in the presence of a condensing agent;

b) cyclizing the serine moiety of the obtained compound of formula IIIa

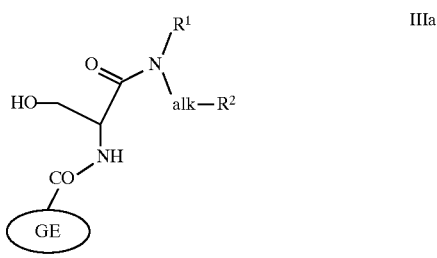

with a suitable cyclizing reactant in order to obtain tha serine-oxazoline cyclization.

According to method A, the chirality of the final compound is determined by the chirality of the serinamide reactant employed, with retention of the configuration of the serine chiral center. Thus, for obtaining the amide derivatives with a chirality corresponding to the natural one, L-serinamides shall be employed.

Inert organic aprotic solvents useful for the condensation reaction according to method A are those solvents which do not unfavorably interfere with the reaction course and are capable of at least partially solubilizing the antibiotic starting material.

Examples of said solvents are organic amides, ethers of glycols and polyols, phosphoramides, sulfoxides. Preferred examples are: dimethylformamide, dimethoxyethane, hexamethylphosphoramide, dimethylsulfoxide, dioxane, and mixtures thereof. Preferably, dimethylformamide (DMF) is employed.

The condensing agent in the present method is one suitable for forming amide bonds in organic compounds and in particular in peptide synthesis.

Representative and preferred examples of condensing agents are ($C_1$–$C_4$)alkyl, phenyl or heterocyclic phosphorazidates such as, diphenyl-phosphorazidate (DPPA), diethyl-phosphorazidate, di(4-nitrophenyl)phosphorazidate, dimorpholyl-phosphorazidate and diphenylphosphorochloridate or benzotriazol-1-yl-oxytripyrrolidinophosphoniumhexa-fluorophosphate (PyBOP). The preferred condensing agent is DPPA.

The condensing agent is generally employed in a slight molar excess, such as from 1.1 to 1.5; preferably the molar excess of condensing agent is 1.2 times the amount of antibiotic GE 2270 starting compound.

According to the present method, the serinamide of formula IV is normally used in a slight molar excess.

In general, a 1 to 1.5 fold molar excess is used, while a 1.2 fold molar excess is preferred.

For the amidation to proceed, it is necessary that the serinamide of formula IV be capable of forming a salt with the carboxy function of the antibiotic starting material. As this could require the use of a higher amount of the serinamide, in such a case it is convenient to add a salt-forming base to the reaction mixture, at least in an equimolecular amount, and preferably a 2 to 3 fold molar excess, with respect to the antibiotic starting material.

Examples of said salt-forming bases are tertiary organic aliphatic or alicyclic amines such as trimethylamine, triethylamine (TEA), N-methyl pyrrolidine or heterocyclic bases such as picoline, and the like.

In addition, the serinamide of formula IV may also conveniently be introduced in the reaction medium as a corresponding acid addition salt, such as hydrochloride, trifluoroacetate, and the like. In fact, at least in some instances, the use of the salified serinamide of formula IV, which is then freed in situ with the above mentioned bases, is preferred, particularly when the salt is more stable than the corresponding free amine. In this case, at least a double molar proportion and preferably a 2 to 3 fold molar excess of a strong base capable of freeing the serinamide of formula IV from its salts, is used. Also in this case, the suitable base is a tertiary organic aliphatic or alicyclic amine like those exemplified above, preferably TEA.

The reaction temperature will vary considerably depending on the specific starting materials and reaction conditions. In general, it is preferred to conduct the reaction at temperatures from 0° C. to room temperature, preferably starting at about 0° C. and allowing the mixture to reach room temperature during the reaction.

Also the reaction time varies considerably depending on the other reaction parameters; in general the condensation is completed in about 5–24 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques. For instance the reaction mixture may be poured into an aqueous basic solution for precipitating the compound of formula IVa as an addition salt. The basic solution should have a pH suitable for precipitating the salt of the desired compound, without modifying its chemical structure. In general, the pH ranges from 8 to 10, and is obtained with an aqueous solution of an inorganic base, such as alkali or alkaline-earth metal hydroxides, carbonates, bicarbonates, and the like. The compound of formula IVa is obtained as a crude, after filtration and evaporation of the above basic solution, as the purification step is preferably accomplished after the cyclization reaction. However, when a purified product is desired, the known per se separation and purification techniques may be employed, which include, for instance, extraction with solvents, precipitation by pH modification, precipitation by addition of non-solvents, etc., in conjunction with further separations and purifications by column chromatography.

Step b) of the present process, i.e. the serine-oxazoline cyclization is performed according to methods known per se in the art.

According to a preferred embodiment, the compound of formula IIIa is reacted with methoxycarbonylsulfamoyltriethylammonium hydroxide, inner salt (Burgess reagent), and the reaction mixture is then refluxed for obtaining the oxazoline cyclization.

More in detail, the obtained compound of formula IIIa is reacted with an excess (about 3:1 to 15:1) of Burgess reagent, in the presence of an organic aprotic oxygenated solvent, for obtaining the corresponding sulfamoyl ester of the Burgess reactant.

Examples of organic aprotic oxygenated solvents are saturated linear or cyclic ethers or glycol ethers. Preferred examples of said solvents are tetrahydrofuran (THF), dioxane. Optionally chlorinated solvents may also be added to the reaction mixture, such as dichloromethane ($CH_2Cl_2$), chloroform, for increasing the solubility of the reactants.

Optionally, a base may also be added to the reaction mixture, for avoiding undesired side-reactions. Examples of suitable bases are tertiary organic aliphatic or alicyclic amines such as trimethylamine, triethylamine (TEA), N-methyl pyrrolidine or heterocyclic bases such as picoline, and the like; preferably TEA is employed.

The reaction temperature will vary considerably depending on the specific starting materials and reaction conditions. In general, it is preferred to conduct the reaction at temperatures of from 180° C. to 30° C., preferably at room temperature.

Also the reaction time varies considerably depending on the other reaction parameters; in general the reaction is completed in about 4 to 20 hours.

Generally, the reaction course is monitored by TLC or preferably by HPLC according to methods known in the art.

After the reaction is completed, a secondary or tertiary alcohol is added to the reaction mixture, for quenching the reaction. Said alcohol should be able to react with the unreacted Burgess reactant and be transformed in olefinic compounds, preferably low boiling olefines. Thus, a secondary or tertiary ($C_3$–$C_5$)alcohol may suitably be employed, such as isopropanol, tert-butanol, 1-methylpropanol, 1,1-dimethyl-propanol, 1,2-dimethyl-propanol, 1-ethylpropanol; preferably, isopropanol is employed.

The reaction mixture is then refluxed for cyclizing the oxazoline. Time and temperature of the reflux will vary mainly depending on the solvents present in the reaction mixture. For instance, if low boiling solvents (e.g. alcohols, chlorinated solvents) are removed before refluxing, higher reflux temperatures are obtained. Thus, depending on the type of solvents present in the refluxing mixture, the temperature will vary from 50° C. to 80° C. In general, as the higher the reflux temperature, the shorter the time, the reflux time will accordingly vary from 20 to 5 hours.

Also in this case, the reaction course is monitored by TLC or preferably by HPLC according to methods known in the art. On the basis of the results of these assays a man skilled in the art will be able to decide when to stop the reflux and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

The starting material of formula III wherein the group GE is such that $W^1$ is phenyl, $W^2$ is hydroxy, $X^1$ is methyl and $X^2$ is methoxymethylene, corresponding to antibiotic GE 2270 factor $A_3$, and the hydrolysis process for preparing it, are disclosed in U.S. Pat. No. 5139778.

Generally, the above mentioned hydrolytic conditions involve the use of mixtures of buffered or unbuffered aqueous acid media and polar organic solvents. The reaction temperature varies depending on factors such as the strength and the concentration of the acid employed, and is generally comprised between −10° C. and 90° C. Also the reaction time varies considerably depending on parameters such as the temperature, the acid strength and its concentration; generally, it may vary from a few minutes to several hours.

In general, when milder hydrolysis conditions are employed, e.g. shorter reaction time and lower temperature or lower acid strength or concentration, antibiotic GE 2270 factor $A_1$ is normally obtained, while stronger hydrolysis conditions yield antibiotic GE 2270 factor $A_2$. To obtain antibiotic GE 2270 factor $A_3$, still more drastic hydrolysis conditions are necessary. Factor $A_2$ may also be converted into factor $A_3$ by basic hydrolysis with diluted alkali.

By following the above procedure, but starting from GE 2270 factor $B_2$, $C_1$, $C_2$ or amythiamicin factor A instead of GE2270 factor A, the respective starting materials of formula III are obtained.

The serinamide of formula IV is prepared according to known per se techniques of peptide synthesys, described in a number of references books like E. Gross and J. Meienhofer "The Peptides", Vol. 3, Academic Press, New York, 1981 and M. Bodanszky and A. Bodanszky "The Practice of Peptide Synthesis, Springer-Verlag, Berlin Heidelberg, 1984.

As a general procedure, a N-protected serine is reacted with the desired amine of formula IVa

wherein $R^1$, alk, and $R^2$ are as defined in formula I. As said above, when amide derivatives of formula I with a chirality corresponding to the natural one are desired, L-serinamides shall be employed; accordingly, the amine of formula IVa shall be reacted with a N-protected L-serine.

As known in the art, the amidation reactions may either be performed in the presence of a condensing agent (e.g. phosphorazidates such as diphenilphosphorazidate, DPPA) or the N-protected amino acid may be reacted in the form of an activated ester (such as pentafluorophenyl, N-hydroxysuccynimide or 1-hydroxybenzothiazole ester).

The protecting group employed in the above described process are those generally employed in peptides synthesis. Preferably, the N-protection of serine is performed with protecting group which are easily removable under acid or neutral hydrolitic conditions, such as t-butoxycarbonyl (BOC) or benzyloxycarbonyl (cbz).

Preferably, the N-deprotection of the serinamide is performed only short before the amidation reaction with the GE2270 starting material, so to avoid the formation of undesired side products.

The amine of general formula IVa is either a commercially available compound or is prepared according to known per se techniques, described in a number of references books, such as "Comprehensive Organic Syhthesis, vol. 8, 1991, Pergamon Press".

Another method (hereinafter defined as "Method B") for preparing the compounds of the invention is to react a compound of formula V

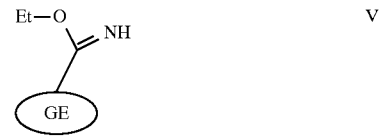

wherein the group GE is as defined in formula I, with a serinamide of formula IV as above defined, in a protic organic solvent.

Also in this case, the chirality of the final compound is determined by the chirality of the serinamide reactant employed, with retention of the configuration of the serine chiral center.

Preferred protic organic solvents are those solvents which do not unfavourably interfere with the reaction course and are capable of at least partially solubilizing the antibiotic starting material. Preferred examples of such solvents are $(C_1-C_4)$alcohols, such as methanol, ethanol, propanol, isopropanol, butanol, isobutanol and mixtures thereof.

Preferably, also minor amounts of an aprotic organic solvent are added, for increasing the solubility of the GE 2270 starting material; preferred solvents are in this case chlorinated solvents, particularly preferred being dichloromethane.

Furthermore, as the serinamide of formula IV is preferably employed in the form of acid addition salt, a base as defined before is preferably added to the reaction mixture. The total amount of base will depend on the number of salified aminic groups of serinamide; as a general rule, if "n" is the number of equivalents of salified aminic groups, then "n−1" equivalents of base are added.

Examples of said bases are, as above, tertiary organic aliphatic or alicyclic amines such as trimethylamine, triethylamine (TEA), N-methyl pyrrolidine or heterocyclic bases such as picoline, and the like, preferred being TEA.

The reaction temperature will vary considerably depending on the specific starting materials and reaction conditions. In general, it is preferred to conduct the reaction at temperatures of from 15° C. to 30° C., conveniently at room temperature.

Also the reaction time varies considerably depending on the other reaction parameters; in general the condensation is completed in about 20–40 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

A suitable method for preparing the starting material of formula V is as described in European Patent Application no. 565567 which has as its equivalent, U.S. Pat. No. 5,599,791, here incorporated by reference. Antibiotic GE 2270 factor $A_2$ (prepared as described in the above cited U.S. Pat. No. 5139778), or the corresponding derivatives of GE2270 factor $B_2$, $C_1$, $C_2$ or amythiamicin factor A, is reacted with ammonia in the presence of an organic protic solvent, preferably $(C_1-C_4)$alcohol, particularly preferred being methanol. After about 2 to 4 days, preferably 3 days, the solution is evaporated and the residue is worked up according to the above known per se techniques, thus obtaining the respective amide derivative of formula:

The obtained compound is in turn reacted with a solution of Burgess reagent in an organic aprotic solvent. Suitable solvents are cyclic or glycol ethers such as THF or dioxane or chlorinated solvents such as dichloromethane ($CH_2Cl_2$) or chloroform, or mixtures thereof; preferably a mixture of $THF/CH_2Cl_2$ is employed.

Furthermore, a base is optionally added to the reaction mixture, as previously described; preferably triethylamine is employed.

Optionally, further Burgess reagent may be added to the reaction mixture after 12 to 20 hours, preferably after 16 hours.

The reaction temperature, depending on the other reaction parameters, may vary from 18° C. to 30° C. preferably at room temperature.

Also the reaction time varies considerably depending on the other reaction parameters; in general the reaction is completed in about 12 to 36 hours after the last addition of Burgess reagent.

Generally, the reaction course is monitored by TLC or preferably by HPLC according to methods known in the art. On the basis of the results of these assays a man skilled in the art will be able to decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent).

The corresponding nitrile derivative of formula

is thus obtained, which is then dissolved in ethanol, preferably in the presence of a chlorinated co-solvent (e.g. dichloromethane, chloroform), and the solution is cooled at about 0° C.; dry HCl is then bubbled through the solution for from 4 to 8 hours, preferably for 6 hours.

The reaction mixture is preferably allowed to stay at about 4° C. for from 10 to 18 hours, and then poured into a buffering basic solution for neutralizing the excess of HCl; such solution, having a pH lower than 10, is generally a phosphate or carbonate buffer, preferably a carbonate buffer, particularly preferred being a saturated aqueous solution of sodium carbonate.

The solid which precipitates is worked up according to the above known per se techniques, thus obtaining the desired starting material of formula V.

A further method for preparing the compounds of the invention (hereinafter defined as "Method C") is to react a compound of formula VI

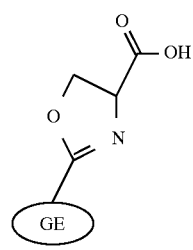

wherein the group GE is as defined in formula I, with an amine of general formula IVa:

wherein $R^1$, alk, and $R^2$ are as defined in formula I, in the presence of an inert organic solvent and of a condensing agent.

Useful inert organic aprotic solvents are as defined for method A.

Also type and amounts of condensing agent are those defined for the condensation reaction of method A.

The starting material of formula VI is preferably used in its salified form, preferably as an alkali metal salt, particularly preferred being the sodium salt. Thus, a strong acid is conveniently added to the reaction mixture, for freeing the compound from its salt; in general a 2 fold excess of acid equivalents are preferably added. Examples of strong acids are hydrohalide acids or sulfuric acid; preferred being hydrochloric acid.

As above, a salt-forming base is preferably added to the reaction mixture; type and amount of such base will vary depending on the parameters defined above (i.e. amount of reacting amine and use of salified amine), as well as on the presence of the above defined strong acid; if said acid is present, at least an equivalent amount of base for each equivalent of acid is further added to the reaction mixture.

The reaction temperature will vary considerably depending on the specific starting materials and reaction conditions.

In general, it is preferred to conduct the reaction at temperatures between 15° C. and 30° C., conveniently at room temperature.

Also the reaction time varies considerably depending on the other reaction parameters. In general the condensation reaction is completed in about 10–16 h.

Generally, the reaction course is monitored by TLC or preferably by HPLC according to methods known in the art. On the basis of the results of these assays a man skilled in the art will be able to evaluate the reaction course and decide when to stop the reaction and start working up the reaction mass according to known per se techniques, which include, as above, extraction with solvents, precipitation by pH modification, precipitation by addition of non-solvents, etc., in conjunction with further chromatographic separations and purifications techniques, such as flash chromatography (e.g. on silica gel using dichloromethane/methanol mixtures as eluent), reverse phase chromatography or chromatography on neutral aluminium oxide (using dichloromethane/methanol mixtures as eluent).

A suitable method for preparing the starting material of formula VI is to react a solution of the starting material of general formula V in ethanol, preferably in the presence of a chlorinated co-solvent (e.g. dichloromethane, chloroform), with a L-serine ($C_1$–$C_4$)alkyl ester salt, preferably methyl ester hydrochloride. The reaction temperature will vary from 15° C. to 30° C., preferably about room temperature, for a time reaction of from 3 to 5 days, preferably about 4 days.

The reaction mixture is then worked up according to known per se techniques, and the solid obtained is purified by means of known chromatographic techniques, preferably by chromatography on silica gel, thus obtaining the compound of formula:

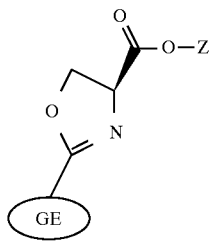

wherein Z represents ($C_1$–$C_4$)alkyl.

The above compound is then dissolved in an inert organic solvent (e.g. alkylamides, alkylnitriles, saturated linear or cyclic ethers, glycol ethers, phosphoramides, chlorinated solvents or mixtures thereof; preferably dioxane) and hydrolyzed with a strong base, such as an alkali or alkaline-earth metal hydroxide, preferably sodium hydroxide, obtaining the corresponding carboxylic acid sodium salt, which may be recovered according to known per se techniques, for instance by addition of non-solvents, preferably ethyl ether.

The so obtained starting material is in general a mixture of two epimers, as the basic hydrolysis normally leads to the epimerization of the chiral center on the oxazoline ring. This mixture may be separated or employed as such for the condensation reaction with the amine, thus obtaining an epimeric mixture of the compounds of the invention.

If desired, the epimeric mixture may be separated (either before or after the condensation reaction) according to known per se techniques, such as by reverse phase HPLC, chromatography on neutral or basic aluminium oxide or HPLC on chiral phases.

The following table lists the structural formula of some representative compounds of the invention, for which antimicrobial activity and preparation methodology are given in the following of the specification. The core molecule of all the compounds, i.e. the group GE, corresponds to antibiotic GE2270 factor A. All the compounds are intended as enantiomeric mixtures (R,S enantiomers), except compounds 4s, 10s, 19s and 21s, which correspond to the S enantiomers.

| Compound No. | $-N\begin{matrix}R^1\\ alk-R^2\end{matrix}$ group |
|---|---|
| 1 | $-NH-CH_2-\underset{N}{\underset{|}{\underset{(CH_2)CH_3}{\phantom{X}}}}$ (pyrrolidine with N-propyl) |
| 2 | $-NH-(CH_2)_2-N$ (pyrrolidine) |
| 3 | $-NH-(CH_2)_2-N(C_2H_5)_2$ |
| 4, 4s | $-N(CH_3)-(CH_2)_2-N(CH_3)_2$ |
| 5 | $-NH-(CH_2)_3-N(CH_3)_2$ |
| 6 | $-N\underset{\phantom{X}}{\diagup\diagdown}N-CH_3$ (piperazine) |
| 7 | $-NH-(CH_2)_2-N(CH_3)_2$ |
| 8 | $-N(C_2H_5)-(CH_2)_2-N(CH_3)_2$ |
| 9 | $-N(C_2H_5)-(CH_2)_2-N(C_2H_5)_2$ |
| 10, 10s | $-N\underset{\phantom{X}}{\diagup\diagdown}\phantom{X}N(CH_3)_2$ (piperidine-4-yl dimethylamino) |
| 11 | $-NH-(CH_2)_2-N(CH(CH_3)_2)_2$ |
| 12 | $-N\underset{\phantom{X}}{\diagup\diagdown}NH$ with CH_3 substituents (2,6-dimethylpiperazine) |
| 13 | $-NH-\underset{NH}{\diagup\diagdown}CONH_2$ (pyrrolidine with CONH2) |
| 14 | $-N(CH_3)-CH_2-CO-N(CH_2)_2-N(CH_3)_2$ <br>                                                 $CH_3$ |
| 15 | $-NH-CH(CH_3)-CO-N(CH_2)_2-N(CH_3)_2$ with CH_3 |
| 16 | $-N(CH_3)-(CH_2)_2-N(CH_2)_2-N(CH_3)_2$ with CH_3 |
| 17 | $-N\underset{\phantom{X}}{\diagup\diagdown}N-(CH_2)_3-N(CH_3)_2$ (piperazine) |

-continued

| Compound No. | $-N\begin{matrix}R^1\\ alk-R^2\end{matrix}$ group |
|---|---|
| 18 | $-N(CH_3)-(CH_2)_2-N\underset{\diagdown\_\_\diagup}{\diagup\overline{\phantom{xx}}\diagdown}N-CH_3$ |
| 19, 19s | $-N(CH_3)-(CH_2)_2-N\underset{\diagdown\_\_\diagup}{\diagup\overline{\phantom{xx}}\diagdown}N-(CH_2)_2-OH$ |
| 20 | $-N\underset{\diagdown\_\_\diagup}{\diagup\overline{\phantom{xx}}\diagdown}N-(CH_2)_2-N\underset{\diagdown\_\_\diagup}{\diagup\overline{\phantom{xx}}\diagdown}O$ |
| 21, 21s | $-N\underset{\diagdown\_\_\diagup}{\diagup\overline{\phantom{xx}}\diagdown}CH_2-N(CH_3)-(CH_2)_2-N(CH_3)_2$ |

The antimicrobial activity of the compounds of the invention can be demonstrated by a series of standard tests in vitro.

The minimal inhibitory concentration (MIC) has been determined by microbroth dilution methodology, in the presence of 0,01% (w/v) of bovine serum albumin (BSA). BSA is added to the diluent to avoid possible adherence of the compounds of the invention to the plastic surface of the microtiter wells, as disclosed also by B. Goldstein et al., Antimicrobial Agents and Chemotherapy, 37 (1993), 741–745.

Inocula were $10^4$ CFU/ml, except for *Propionibacterium acnes* and *Bacteroides fragilis* ($10^5$ CFU/ml) MICs were read after 18–24 h, except for *Haemophilus influenzae, P. acnes, B. fragilis* (48 h).

All microorganisms were incubated at 37° C.; *H. influenzae* in a 5% $CO_2$ atmosphere, anaerobes in a $N_2$—$CO_2$—$H_2$ (80:10:10) mixture; other organisms in air.

The growth media are: Oxoid Iso-Sensitest broth for staphylococci and *Enterococcus faecalis*); Difco Todd Hewitt broth for streptococci; Difco brain heart infusion broth+1% Difco Supplement C. for *H. influenzae;* Difco Wilkins-Chalgren broth for anaerobes.

MICs for some microorganisms are reported below in Table I.

TABLE 1

| STRAIN | Internal code | MIC of the compounds (μg/ml) |||||||| 
|---|---|---|---|---|---|---|---|---|---|
| | | 1 | 2 | 3 | 4 | 4s | 5 | 6 | 7 |
| *Staphylococcus aureus* | L165 | 0.06 | 0.06 | 0.06 | 0.06 | 0.06 | 0.06 | 0.06 | 0.13 |
| *Staph. epidermidis* ATCC 12228 | L147 | n.t. | n.t. | n.t. | 0.06 | 0.06 | n.t. | n.t. | n.t. |
| *Staph. haemolyticus* | L602 | n.t. | n.t. | n.t. | 0.06 | 0.06 | n.t. | n.t. | n.t. |
| *Streptococcus pyogenes* | L49 | 2 | 1 | 2 | 0.5 | 1 | 1 | 4 | 4 |
| *Strept. pneumoniae* | L44 | 0.25 | 0.25 | 0.5 | 0.13 | 0.25 | 0.25 | 0.25 | 1 |
| *Strept. sanguis* | L1721 | 0.5 | 0.5 | 0.5 | 0.13 | 0.13 | 0.25 | 0.25 | 1 |
| *Strept. agalactiae* | L310 | 2 | 4 | 4 | 0.5 | 0.5 | 2 | 4 | 8 |
| *En.t.erococc. faecalis* ATCC 7080 | L149 | n.t. | n.t. | n.t. | 0.016 | 0.016 | n.t. | n.t. | n.t. |
| *Propionibact. acnes* ATCC 6919 | L1014 | n.t. | n.t. | n.t. | 0.016 | 0.03 | n.t. | n.t. | n.t. |
| *Bacteroides fragilis* ATCC 25285 | L1011 | n.t. | n.t. | n.t. | 8 | 8 | 32 | 128 | n.t. |
| *Haemoph. influenzae* ATCC 19418 | L970 | 128 | 128 | 128 | 4 | 64 | n.t. | n.t. | n.t. |

| STRAIN | Internal code | MIC of the compounds (μg/ml) |||||||| 
|---|---|---|---|---|---|---|---|---|---|
| | | 8 | 9 | 10 | 10s | 11 | 12 | 13 | 14 |
| *Staphylococcus aureus* | L165 | 0.06 | 0.06 | 0.06 | 0.03 | 0.13 | 0.06 | 0.13 | 0.06 |
| *Staph. epidermidis* ATCC 12228 | L147 | n.t. | n.t. | n.t. | 0.06 | n.t. | n.t. | 0.5 | n.t. |
| *Staph. haemolyticus* | L602 | n.t. | n.t. | n.t. | 0.13 | n.t. | n.t. | 0.5 | n.t. |
| *Streptococcus pyogenes* | L49 | 8 | 2 | 2 | 1 | 8 | 2 | 4 | 2 |
| *Strept. pneumoniae* | L44 | 0.5 | 0.5 | 0.25 | 0.5 | 2 | 0.5 | 0.5 | 0.25 |
| *Strept. sanguis* | L1721 | 1 | 1 | 0.5 | 0.5 | 4 | 0.5 | n.t. | 0.25 |
| *Strept. agalactiae* | L310 | 4 | 32 | 4 | 2 | >128 | 4 | n.t. | 4 |
| *En.t.erococc. faecalis* ATCC 7080 | L149 | n.t. | n.t. | n.t. | 0.03 | n.t. | n.t. | 0.06 | n.t. |
| *Propionibact. acnes* ATCC 6919 | L1014 | n.t. | n.t. | n.t. | 0.016 | n.t. | n.t. | 0.13 | n.t. |
| *Bacteroides fragilis* ATCC 25285 | L1011 | n.t. | n.t. | n.t. | 8 | n.t. | n.t. | >128 | n.t. |
| *Haemoph. influenzae* ATCC 19418 | L970 | n.t. | n.t. | n.t. | 8 | n.t. | n.t. | 128 | n.t. |

TABLE 1-continued

| STRAIN | In.t.ern al code | MIC of the compounds (μg/ml) | | | | | | | | |
|---|---|---|---|---|---|---|---|---|---|---|
| | | 15 | 16 | 17 | 18 | 19 | 19s | 20 | 21 | 21s |
| *Staphylococcus aureus* | L165 | 0.06 | 0.06 | 0.06 | 0.06 | 0.06 | 0.06 | 0.06 | 0.06 | 0.06 |
| *Staph. epidermidis* ATCC 12228 | L147 | n.t. | n.t. | n.t. | n.t. | 0.13 | 0.06 | n.t. | n.t. | 0.06 |
| *Staph. haemolyticus* | L602 | n.t. | n.t. | n.t | n.t. | 0.13 | 0.13 | n.t. | n.t. | 0.016 |
| *Streptococcus pyogenes* | L49 | 4 | 2 | 2 | 2 | 1 | 1 | 4 | 1 | 0.5 |
| *Strept. pneumoniae* | L44 | 0.25 | 0.25 | 0.5 | 0.25 | 0.13 | 0.13 | 0.5 | 0.25 | 0.13 |
| *Strept. sanguis* | L1721 | 0.5 | 0.25 | 0.5 | 0.25 | 0.13 | n.t. | 1 | 0.25 | n.t. |
| *Strept. agalactiae* | L310 | 4 | 8 | 8 | 4 | 2 | n.t. | >128 | 4 | n.t. |
| *En.t.erococc. faecalis* ATCC 7080 | L149 | n.t. | n.t. | n.t. | n.t. | 0.016 | 0.016 | n.t. | n.t. | 0.03 |
| *Propionibact. acnes* ATCC 6919 | L1014 | n.t. | n.t. | n.t. | n.t. | 0.016 | 0.016 | n.t. | n.t. | 0.016 |
| *Bacteroides fragilis* ATCC 25285 | L1011 | n.t. | n.t. | n.t. | n.t. | 4 | 8 | n.t. | n.t. | 8 |
| *Haemoph. influenzae* ATCC 19418 | L970 | n.t. | n.t. | n.t. | n.t. | 16 | 8 | n.t. | n.t. | 8 |

In view of their properties, the compounds of the invention can be used as active ingredients in the preparation of medicaments for human or animal treatment.

In particular, the amide derivatives of antibiotic GE 2270 of formula I are antimicrobial agents mainly active against gram positive bacteria.

The main therapeutic indication of the antibiotic substances of the invention is thus in the treatment of infections related to the presence of microorganisms susceptible to them.

The term "treatment" is intended to encompass also prophylaxis, therapy and cure.

The patient receiving this treatment is any animal in need, including primates, in particular humans, and other mammals such as equines, cattle, swine, sheep, poultry and pets in general.

The compounds of the invention can be administered as such or in admixture with pharmaceutically acceptable carriers and can also be administered in conjunction with other antimicrobial agents. Conjunctive therapy, thus includes sequential, simultaneous and separate administration of the active compounds in a way that the therapeutical effects of the first administered one is not entirely disappeared when the subsequent is administered.

The dosage of the active ingredient depends on many factors which include type, age and conditions of the patient, specific active ingredient and formulation selected for administration, administration schedule, etc.

Experimental tests for determining the sensitivity of the microorganisms isolated from the patient may also offer useful indication to select the appropriate dosage.

In general, effective antimicrobial dosages are employed per single unit dosage form.

Repeated applications of these dosage forms, e.g. from 2 to 6 times a day, are in general preferred. An effective dosage may be in general in the range 0.5–50 mg/kg body weight/day.

Anyway, the prescribing physician will be able to determine the optimal dosage for a given patient in a given situation.

The compounds of the invention can be formulated into formulation suitable for parenteral administration containing a liquid vehicle, according to procedures known per se in the art. Examples of suitable vehicles for preparing injectable dosage forms of the compounds of the invention are water, aqueous vehicles (e.g. Dextrose injections), water miscible solvents (e.g. ethyl alcohol, polyethylene glycol, propylene glycol, etc.) and non-aqueous vehicles (e.g. "fixed oils" such as corn oil, cottonseed oil, peanut oil and sesame oil). Optionally, the injectable preparation may further contain surface-active agent (e.g. polyoxyethylene sorbitan monooleate or polyethoxylated castor oil), buffers for stabilizing the solution (e.g. citrates, acetates and phosphates) and/or antioxidants (e.g. ascorbic acid or sodium bisulfite).

For instance, a typical formulation for parenteral administration may contain from 5 to 50 mg of a compound of the invention for ml of final preparation. The compound will generally be formulated in water for injection, optionally in admixture with 10–20% of a surface-active agent which may be a polyoxyethylene sorbitan fatty acid ester, a polyoxyethylene castor oil derivative or a polyoxyethylene hydrogenated castor oil derivative and 0–20%; optionally, the formulation may further contain 10–20% of a solubilizing agent such as propylene glycol, dimethylacetamide, dimethylformamide, ter-butyl-N-hydroxycarmabate, 1,2-, 1,3-or 1,4-butandiol, ethyl oleate, tetrahydrofurfuryl-polyethylene-glycol 200, dimethyl isosorbide, benzyl alcohol and the like. A preferred solubilizing agent is propylene glycol.

Polyoxyethylene sorbitan fatty acid esters are commercially available and some of them are traded under the trade name "Tween". They are also known with the non-proprietary name of "polysorbates". Examples of them are polysorbate 20, 21, 40, 60, 61, 65, 80, 81 and 85. Preferred for use in the formulations of the invention is polysorbate 80 (sorbitan mono-9-octadecenoate, poly(oxy-1,2-ethanediyl) derivatives).

Polyoxyethylene castor oils and polyoxyethylene hydrogenated castor oils are also commercially available. Some of them are traded with the trade name "Cremophor". Examples of such compounds are those known as Cremophor EL (polyethoxylated castor oil), Cremophor RH 40 (polyethoxylated hydrogenated castor oil), Cremophor RH 60 (PEG 60 hydrogenated castor oil) or Emulphor EL-719 (polyoxyethylated vegetable oil).

If necessary, the pH of the preparation may be adjusted with a suitable buffering agent; conveniently, TRIS (i.e.trihydroxymethylaminomethane), phosphate or acetate buffers can be used.

A particularly preferred formulation for parenteral administration is one containing the compound of the invention in the salified form dissolved in distilled water, without any excipients.

An example of such a preparation is the following

| Compound 4s | 50 mg |
|---|---|
| Water for injection | 1 ml |
| pH 5 with acetic acid | |

Care should be taken to set the pH at a volume of about 5 for helping the solubilization of the product, but not however than 4.5 because possible hydrolysis of the oxazoline ring of the molecule may occur.

Examples of formulations of the compounds of the invention in admixture with suitable excipients, for parenteral administration, are the following:

| A) compound 4s | 100 mg |
|---|---|
| propylene glycol | 1 ml |
| water for injection q.s. | 5 ml |
| phosphate buffer pH 8–8.5 | |
| B) compound 4s | 50 mg |
| Cremophor RH 40 | 1 g |
| water for injection q.s. | 10 ml |
| phosphate buffer pH 8–8.5 | |

A further pharmaceutical formulation is represented by a formulation suitable for a topical application on an intact or damaged skin or mucous membrane. Examples of such formulations are powders, ointments, creams and lotions. The excipients in these formulations are the usual pharmaceutically acceptable vehicles such oleaginous ointment bases (e.g. cetyl esters wax, oleic acid, olive oil, paraffin, spermaceti, starch glycerite); absorbent ointment bases (e.g. anhydrous lanolin, hydrophylic petrolatum), emulsion ointment bases (e.g. cetyl alcohol, glyceryl monostearate, lanolin, stearic acid), water-soluble ointment bases (e.g. glycol ethers and their derivatives which include polyethylene glycols, poly(oxy-1,2-ethan ediyl)-alpha-hydro-omega-hydroxy-octadecanoate, polysorbates, and polyethylene glycols mono-stearates).

These formulations may contain other known excipients, such as preservatives and are prepared as known in the art and reported in reference handbooks such as Remington's Pharmaceutical Sciences, Seventeenth edition, 1985, Mack Publishing Co.

A preferred topic preparation is an ointment containing from 1% to 10% of a compound of the present invention.

Besides their use as medicaments in human and veterinary therapy, the compounds of the invention can also be used as animal growth promoters.

For this purpose, a compound of the invention is administered orally in a suitable feed. The exact concentration employed is that which is required to provide for the active agent in a growth promotant effective amount when normal amounts of feed are consumed.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed.

The way in which such feed premixes and complete rations can be prepared and administered are described in reference books, such as "Applied Animal Nutrition", W. H. Freedman and CO., S. Francisco, USA, 1969 or "Livestock Feeds and Feeding" O and B books, Corvallis, Oreg., USA, 1977.

For better illustrating the invention, the following examples are given.

EXAMPLES

METHOD A—Reaction of GE2270 factor $A_3$ (see preparation no. 3) with the selected L-serinamide and subsequent cyclization

Example A1

Preparation of compound 10s

To a solution of GE2270 factor $A_3$ (1 mmol) in DMF (10 ml) and TEA (2.2 mmol), DPPA (1.2 mmol) is added with stirring at 0° C. The temperature is allowed to rise to room temperature and after 4.5 h a solution of the hydrochloric salt of the selected L-serinamide (1.2 mmol) and TEA (3 mmol) in DMF (3 ml) is added with stirring. The reaction is allowed to stir overnight at room temperature and then poured in aqueous 0.06M $NaHCO_3$ (200 ml). The precipitate is collected by filtration, allowed to dry in the air and then purified by flash chromatography on silica gel 60 (400–230 mesh) using $CH_2Cl_2$ containing from 4% to 10% MeOH as the eluant. For facilitating elution, TEA from 0.1% to 1% (v/v) can be added to the eluant. Fractions containing the condensation product are combined and the solvent evaporated. Thorough washing of the obtained solid with ethyl ether yields the condensation product as a fine powder.

A solution of methoxycarbonylsulfamoyl-triethylammonium hydroxide, inner salt (Burgess reagent) (5 mmol) in dry $CH_2Cl_2$ (3 ml) is added dropwise in an argon atmosphere at room temperature over 6 h to a stirred solution of the above condensation product (1 mmol) in dry tetrahydrofuran (THF) (30 ml). At the end of the addition of the Burgess solution, the disappearance of the condensation product and the formation of a more formation of a more hydrophilic adduct is controlled by HPLC; then, isopropanol (30 ml) is added to quench the excess of reagent. Stirring is continued for 2 h at room temperature and then the reaction mixture is refluxed (about 70° C.) for 6 h to cyclize the oxazoline ring. After evaporation of the solvent under reduced pressure, the crude reaction mixture is purified on neutral aluminum oxide grade I (Merck) using from 2.5% to 5% MeOH in $CH_2Cl2$ as the eluant. Fractions containing the title compound are combined and the solvent evaporated to dryness under reduced pressure to yield a solid which is further purified by flash chromatography on silica gel 60 (400–230 mesh) using $CH_2Cl_2$ containing from 4% to 10% MeOH as the eluant. For facilitating elution, TEA from 0.1% to 1% (v/v) can be added to the eluant. Fractions containing the title compound are combined and the solvent evaporated. Thorough washing of the solid with ethyl ether yields the title compound as a fine powder.

Example A2

Preparation of compound 21s

To a solution of GE2270 factor $A_3$ (1 mmol) in DMF (10 ml) and TEA (2.2 mmol), DPPA (1.2 mmol) is added with stirring at 0° C. The temperature is allowed to rise to room temperature and after 4.5 h a solution of the hydrochloric salt of the selected L-serinamide (1.2 mmol) and TEA (3 mmol) in DMF (3 ml) is added with stirring. The reaction mixture is allowed to stir overnight at room temperature and then poured in aqueous 0.06M $NaHCO_3$ (200 ml). The precipitate is collected by filtration, allowed to dry in the air and then purified by flash chromatography on silica gel 60 (400–230 mesh) using $CH_2Cl_2$ containing from 4% to 10% MeOH as eluant. For facilitating elution, TEA from 0.1% to 1% (v/v) can be added to the eluant. Fractions containing the condensation product are combined and the solvent evaporated. Thorough washing of the solid with ethyl ether yields the condensation product as a fine powder.

Burgess reagent (4 mmol) and TEA (4 mmol) are added in an argon atmosphere at room temperature with stirring to a solution of the above condensation product (1 mmol) in dry $CH_2Cl_2$ (30 ml). After 20 min dry THF (30 ml) is added to allow the reaction to begin and stirring is continued at room temperature for 13 h. After addition of isopropanol (25 ml) to react the excess of Burgess reagent, the reaction is refluxed (about 56° C for 18 h to cyclize the oxazoline ring. After evaporation of the solvent under reduced pressure, the crude reaction mixture is purified on neutral aluminum oxide grade I (Merck) using from 2.5% to 5% MeOH in $CH_2Cl_2$ as the eluant. Fractions containing the title compound are combined and the solvent evaporated to dryness under reduced pressure to yield a solid which is further purified by flash chromatography on silica gel 60 (400–230 mesh) using $CH_2Cl_2$ containing from 4% to 10% MeOH as the eluant. For facilitating elution, TEA from 0.1% to 1% (v/v) can be added to the eluant. Fractions containing the title compound are combined and the solvent evaporated. Thorough washing of the solid with ethyl ether yields the title compound as a fine powder.

METHOD B—Reaction of starting material GE III (see preparation no. 6) with L-serinamide (see preparation no. 18)

Example B1

Preparation of compounds 4s, 10s, 19s, 21s

To a solution of starting material GE-II (1 mmol) in absolute ethanol (35 ml), $CH_2Cl_2$ (3.5 ml) and TEA (3 or 6 mmol), L-serinamide prepared according to preparation 18 (3 mmol) is added with stirring at room temperature. After about 30 h, the reaction mixture is poured in aqueous 0.06M $NaHCO_3$ (100 ml) and the solid formed is isolated by centrifugation, washed with more water and then taken up in $CH_2Cl_2$ containing a few drops of methanol. The solution is dried over $Na_2SO_4$ and the solvent is evaporated under reduced pressure to yield a solid which is chromatographed on neutral aluminum oxide grade I (Merck) using from 2.5% to 5% MeOH in $CH_2Cl_2$ as eluant. Fractions containing the title compound are combined and the solvent evaporated to dryness under reduced pressure to yield a solid which is further purified by flash chromatography on silica gel 60 (400–230 mesh) using $CH_2Cl_2$ containing from 4% to 10% MeOH as eluant. Optionally from 0.1% to 1% TEA is added to the eluant. Fractions containing the title compound are combined and the solvent evaporated. Thorough washing of the obtained solid with ethyl ether yields the title compound as a fine powder.

METHOD C—Reaction of starting material GE V (see preparation no. 8) with the selected amine Example C1

Preparation of compound 10

To a stirred solution of the sodium salt of compound GE V (1 mmol) in DMF (30 ml), TEA (4 mmol) and aqueous 1N HCl (2 mmol) are added at room temperature. After a couple of minutes, the selected amine (1.5 mmol) and DPPA (1.2 mmol) are added thereto and stirring is continued overnight. The reaction mixture is then poured into water (150 ml) and the solid which forms is isolated by centrifugation, washed with water and then took up in $CH_2Cl_2$ containing a few drops of methanol. The solution is dried over $Na_2SO_4$ and the solvent is evaporated under reduced pressure to yield a solid which is chromatographed on neutral aluminum oxide grade I (Merck) using from 2.5% to 5% MeOH in $CH_2Cl_2$ as the eluant. Fractions containing the title compound are combined and the solvent evaporated. Thorough washing of the obtained solid with ethyl ether yields the title compound as a fine powder.

Example C2

Preparation of compounds 1 to 21 (epimers mixture)

To a stirred solution of the sodium salt of compound GE V (0.1 mmol) in DMF (9.7 ml), TEA (0.4 mmol) and aqueous 1N HCl (0.2 mmol) are added at room temperature. After a couple of minutes, a 0.2M DMF solution of the selected amine (0.2 mmol) and a 0.12M DMF solution of DPPA (0.14 mmol) are added at the same temperature and stirring is continued overnight.

Example C3

Preparation of compound 13

The reaction is substantially carried out as described in Example C1. Once the reaction product has been purified by flash chromatography, the solid obtained (1 mmol) is treated with cold trifluoroacetic acid (TFA) (7 ml). The suspension is swirled for a few minutes until a solution is obtained and TFA is evaporated under reduced pressure in the cold. The gummy product still containing traces of TFA is then treated with ethyl ether and the trifluoroacetate salt of the title compound obtained as a fine powder.

The compounds obtained according to the above examples have been characterized by their HPLC retention times, according to the following methodology, "HPLC-1":

Column: RP18 (Merck) 5 plm

Eluent: Phase A: ammonium formiate 0.05M;
Phase B: acetonitrile

| Gradient: | minutes | 0 | 2 | 15 | 25 |
|---|---|---|---|---|---|
| | % B | 40 | 40 | 80 | 80 |

Flow rate: 0.7 ml/min

Detection: UV at 254 nm and 310 nm.

The retention times of compounds 10s, 19 and 19s have also been determined according to the following methodology, "HPLC-2":

Column: Supelcosil LC 3DP (Supelco) 5 µm

Eluent: Phase A: [AcONa (1.3 g/l):LiCl (1.2 g/l)]: acetonitrile 95:5, pH 5 (AcOH);
Phase B: [AcONa (1.3 g/l):LiCl (1.2 g/l)]: acetonitrile 30:70, pH 5 (AcOH)

| Gradient: | minutes | 0 | 10 | 30 | 40 | 45 | 55 |
|---|---|---|---|---|---|---|---|
| | % B | 30 | 40 | 50 | 60 | 70 | 90 |

Flow rate: 1.5 ml/min

Detection: UV at 254 nm.

The retention times of compounds 4, 4s and 21s have also been determined according to the following methodology, "HPLC-3":

Column: Supelcosil LC 3DP (Supelco) 5 µm

Eluent: Phase A: [AcONa (1.3 g/l):LiCl (1.2 g/l)]: acetonitrile 95:5, pH 5 (AcOH)
Phase B: [AcONa (1.3 g/l):LiCl (1.2 g/l)]: acetonitrile 30:70, pH 5 (AcOH)

| Gradient: | minutes | 0 | 10 | 40 | 45 | 90 |
|---|---|---|---|---|---|---|
| | % B | 40 | 40 | 50 | 50 | 90 |

Flow rate: 1.5 ml/min
Detection: UV at 254 nm.
Retention times determined according to methodology HPLC-1

| Compound | Retention time | Compound | Retention time |
|---|---|---|---|
| 1 | 12.6; 12.9 | 12 | 12.5 |
| 2 | 12.5 | 13 | 12.6 |
| 3 | 12.8 | 14 | 11.4 |
| 4 | 13.7 | 15 | 11.7 |
| 4s | 13.7 | 16 | 14.8 |
| 5 | 11.6 | 17 | 13.7 |
| 6 | 13.4 | 18 | 13.3; 14.4 |
| 7 | 12.3 | 19 | 10.0 |
| 8 | 14.4 | 19s | 10.0 |
| 9 | 15.9 | 20 | 12.4 |
| 10 | 13.3 | 21 | 15.1 |
| 10s | 13.3 | 21s | 15.1 |
| 11 | 14.2 | | |

Retention times determined according to methodology HPLC-2

| Compound | Retention time |
|---|---|
| 10s | 30.09 |
| 19 | 28.17; 30.33 |
| 19s | 28.17 |

Retention times determined according to methodology HPLC-3

| Compound | Retention time |
|---|---|
| 4 | 28.07; 30.96 |
| 4s | 28.07 |
| 21s | 32.85 |

Compounds 4, 4s, 10, 10s, 13, 19, 19s and 21s have also been characterized by means of $^1$H-NMR spectra, FAB-MS spectra and UV spectra; methodologies and data are reported hereinafter.

The $^1$H-NMR spectra were recorded with a Bruker AM500 or AMX 600 spectrometer using DMSO-$d_6$ (hexadeuterodimethylsulfoxide) as solvent (s=singlet, br=broad singlet, d=doublet, dd=doublet of doublets, t=triplet, m=multiplet)

Compound 4
$^1$H—N.M.R. (DMSOd$_6$) δ(ppm): 0.85(d, 3H); 0.88(d, 3H); 1.37(dd, 1H); 2.17(m, 4H); 2.26(s, 3H); 2.49(d, 3H); 2.59(s, 3H); 2.72(dd, 1H); 3.3, 3.6–3.5, 4.0–3.9(m, 4H); 3.39(s, 3H); 3.79(dd, 1H); 4.28(dd, 1H); 4.54(dd, 1H); 4.87(m, 1H); 4.98(s, 2H); 5.01(dd, 1H); 5.30(m, 2H); 5.25 (dd, 1H); 5.20(dd, 1H); 6.02(d, 1H); 7.38–7.23(m, 7H); 8.29(m, 2H); 8.43(m, 2H); 8.54, 8.53(s, s, 1H); 8.60(s, 1H); 8.68(m, 2H); 9.00(d, 1H).

Compound 4s
$^1$H-N.M.R. (DMSOd6) δ(ppm): 0.87(d, 3H); 0.90(d, 3H); 1.49(dd, 1H); 2.20(m, 1H); 2.23(s, 3H); 2.30(s, 3H); 2.46(d, 3H); 2.59(s, 3H); 2.70(dd, 1H); 2.92, 3.28(s, s, 3H); 3.39(s, 3H); 3.48–3.33(m, 2H); 3.65–3.48(m, 2H); 3.80(dd, 1H); 4.31(dd, 1H); 4.54(t, 1H); 4.86(m, 1H); 4.99(s, 2H); 5.04 (dd, 1H); 5.18(dd, 1H); 5.28(m, 3H); 5.88(d, 1H); 7.41–7.20 (m, 7H); 8.24(s, 1H); 8.32–8.27(m, 2H); 8.38(d, 1H); 8.48(s, 1H); 8.55(s, 1H); 8.60(d, 1H); 8.65(d, 1H); 8.83(d, 1H).

Compound 10
$^1$H—N.M.R. (DMSOd$_6$) δ(ppm) 0.84(d, 3H); 0.87(d, 3H); 1.75–1.25(m, 4H); 2.00–1.75(m, 2H); 2.15(m, 1H); 2.19(s, 3H); 2.21(s, 3H); 2.37 (m, 1H); 2.47(d, 3H); 2.57(s, 3H) 2.75–2.65(m, 2H); 3.37(s, 3H); 3.78(dd, 1H); 4.27(dd, 1H); 4.35(m, 2H); 4.51(dd, 1H); 5.00–4.90(m, 4H); 5.36–5.17(m, 4H); 6.02(d, 1H); 7.35–7.21(m, 7H); 8.27(m, 2H); 8.41(m, 2H); 8.51(s, 1H); 8.59(s, 1H); 8.67(m, 2H); 8.98(d, 1H).

Compound 10s
$^1$H—N.M.R. (DMSOd6) δ(ppm): 0.84(d, 3H); 0.87(d, 3H); 1.75–1.25 (m, 4H); 1.95–1.75(m, 2H); 2.37–2.16(m, 1H); 2.18(s, 3H); 2.21(s, 3H); 2.37(m, 1H); 2.49(d, 3H); 2.56(s, 3H); 2.72–2.68(m, 2H); 3.37(s, 3H); 3.78(dd, 1H); 4.27(dd, 1H); 4.36(m, 2H); 4.51(dd, 1H); 4.90(m, 1H); 4.97(s, 2H); 5.00(dd, 1H); 5.19(dd, 1H); 5.25(dd, 1H); 5.74–5.29(m, 2H); 6.01(d, 1H); 7.36–7.21(m, 7H); 8.26(m, 1H); 8.28(s, 1H); 8.42(m, 2H); 8.51(s, 1H); 8.59(s, 1H); 8.67(m, 2H); 8.98(d, 1H).

Compound 13
$^1$H—N.M.R. (DMSOd$_6$) δ(ppm): 0.84(d, 3H); 0.87(d, 3H); 1.36(dd, 1H); 2.20(m, 1H); 2.47(d, 3H); 2.58(s, 3H); 2.75–2.60(m, 2H); 3.00(d, 1H); 3.38(s, 3H); 3.77(d, 1H); 4.22–4.0(m, 3H); 4.27(dd, 1H); 4.36(br, 1H); 4.65(dd, 1H); 4.85(dd, 1H); 4.97(s, 2H); 5.00(d, 1H); 5.38–5.15(m, 4H); 6.03(br, 1H); 7.4–7.16(m, 8H); 7.65(br, 1H); 7.90(br, 1H); 8.25(d, 1H); 8.29(s, 1H); 8.42(m, 2H); 8.55(s, 1H); S.60(s, 1H); 8.67 (m, 2H); 9.03(d, 1H).

Compound 19
$^1$H—N.M.R. (DMSOd$_6$) δ(ppm): 0.84(d, 3H); 0.87(d, 3H); 1.34(dd, 1H); 2.16(m, 1H); 2.46(d, 3H); 2.58(s, 3H); 2.65–2.25(m, 10H); 2.69(dd; 1H); 3.29, 2.91(s, s, 3H); 3.38(s, 3H); 3.6–3.25(m, 4H); 3.76(dd, 1H); 3.95 (m, 1H); 4.26(dd, 1H); 4.32(m, 1H); 4.5(m, 1H); 4.9(m, 1H); 4.97(s, 2H); 5.00(dd, 1H); 5.20(dd, 1H); 5.25(dd, 1H); 5.30(m, 2H); 6.01(d, 1H); 7.4–7.2(m, 7H); 8.27(m, 2H); 8.4(m, 2H); 8.51(s, 1H); &.59(s, 1H); 8.67(m, 2H); 8.99(d, 1H).

Compound 19s
$^1$H—N.M.R. (DMSOd$_6$) δ(ppm): 0.84(d, 3H); 0.87(d, 3H); 1.36(dd, 1H); 2.15(m, 1H); 2.46(d, 3H); 2.58(s, 3H); 2.60–2.26(m, 10H); 2.71(dd, 1H); 3.30, 2.89(s, s, 3H); 3.38(s, 3H); 3.58–3.22(m, 4H); 3.76(dd, 1H); 4.95(m, 1H); 4.26(dd, 1H); 4.30(m, 1H); 4.52(m, 1H); 4.91(m, 1H); 4.97(s, 2H); 5.00(dd, 1H); 5.20(dd, 1H); 5.25(dd, 1H); 5.30(m, 2H); 6.01 (d, 1H); 7.44–7.21 (m, 7H); 8.27 (m, 2H); 8.41(m, 2H); 8.51(s, 1H); 8.60(s, 1H); 8.68(m, 2H); 9.00(d, 1H).

Compound 21s
$^1$H—N.M.R. (DMSOd$_6$) δ(ppm): 0.85(d, 3H); 0.88(d, 3H) 1.32(dd, 1H); 2.03–1.82(m, 4H); 2.16(s, 3H); 2.19(s, 3H); 2.22(s, 3H); 2.47(d, 3H); 2.59(s, 3H); 2.65–2.15(m, 7H); 2.72(dd, 1H); 3.39(s, 3H); 3.72(m, 1H); 3.80(dd, 1H); 3.91(m, 1H); 4.07(m, 1H); 4.28(dd, 1H); 4.52(dd, 1H); 4.81(dd, 1H); 4.99(s, 2H); 5.01(d, 1H); 5.15(t, 1H); 5.20(dd, 1H); 5.25(t, 1H); 5.30(dd, 1H); 6.08(br, 1H); 7.41–7.20(m, 7H); 8.29(m, 2H); 8.43(m, 2H); 8.54(s, 1H); 8.60(s, 1H); 8.69(m, 2H); 9.03(d, 1H).

The MS spectra were obtained with a triple stage quadrupole spectrometer TSQ 700 Finningan.
Compound 4 FAB-MS m/z 1278 (MH$^+$, 100%)
Compound 4s FAB-MS m/z 1278 (MH$^+$, 100%)
Compound 10 FAB-MS m/z 1304 (MH$^+$, 100%)
Compound 10s FAB-MS m/z 1304 (MH$^+$, 100%)

Compound 13 FAB-MS m/z 1305 (MH+, 100%)
Compound 19 FAB-MS m/z 1363 (MH+, 100%)
Compound 19s FAB-MS m/z 1363 (MH+, 100%)
Compound 21s FAB-MS m/z 1361 (MH+, 100%)

The UV absorption spectra were recorded with a Perkin-Elmer spectrophotometer Mod. Lamda 16 (200–800 nm).
Compound 4 UV (MeOH) $\lambda_{max}$=310 (E1%, 1 cm=253.8)
Compound 4s UV (MeOH) $\lambda_{max}$=310 (E1%, 1 cm=259.2)
Compound 10 UV (MeOH) $\lambda_{max}$=310 (E1%, 1 cm=240.1)
Compound 10s UV (MeOH) $\lambda_{max}$=310 (E1%, 1 cm=248.4)
Compound 13 UV (MeOH) $\lambda_{max}$=310 (E1%, 1 cm=236.4)
Compound 19 UV (MeOH) $\lambda_{max}$=309 (E1%, 1 cm=237.9)
Compound 19s UV (MeOH) $\lambda_{max}$=309 (E1%, 1 cm=240.3)
Compound 21s UV (MeOH) $\lambda_{max}$=311 (E1%, 1 cm=242.9)

PREPARATION OF STARTING MATERIALS

Preparation of Antibiotic GE2270 Starting Materials

Preparation 1: GE2270 factor A

GE2270 factor A is prepared by fermentation of *Planobispora rosea* ATCC 53773, as described in U.S. Pat. No. 5202241. Recovery and isolation of the factor are as described therein.

Preparation 2: GE2270 factor $A_2$

4'-de[4-[[2-(aminocarbonyl)-1-pyrrolidinyl]
carbonyl]-4,5-dihydro-2-oxazolyl]4'-[[(octahydro-1,
4-dioxopyrrolo-[1,2-a]pyrazin-3-yl)methoxy]
carbonyl]
GE2270 factor A GE2270 factor $A_2$ is prepared by controlled acid hydrolysis from GE2270 factor A, as described in U.S. Pat. No. 5139778.

Preparation 3: GE2270 factor $A_3$

4'-carboxy-4'-de[4-[[2-(aminocarbonyl)-1-
pyrrolidinyl]-carbonyl]-4,5-dihydro-2-oxazolyl]
GE2270 factor A GE2270 factor $A_2$ is prepared by controlled basic hydrolysis from GE2270 factor $A_2$, as described in U.S. Pat. No. 5139778.

Preparation 4: compound GE I

4'-(aminocarbonyl)-4'-de[4-[[2-(aminocarbonyl)-1-
pyrrolidinyl]carbonyl]-4,5-dihydro-2-oxazolyl]
GE2270 factor A Antibiotic GE 2270 factor $A_2$ (1 mmol) is dissolved in a saturated solution of $NH_3$ in methanol (10 ml). The solution is allowed to stand for 3 days at room temperature and then is evaporated under reduced pressure. The residue is taken up in methanol (2 ml) and the title compound precipitated with water, filtered and allowed to dry in air. Thorough washing with ethyl ether yields the title compound (GE-I) of factor A as a white powder.

Preparation 5: compound GE II

4'-cyano-4'-de[4-[[2-(aminocarbonyl)-1-pyrrolidinyl]
-carbonyl]-4,5-dihydro-2-oxazolyl]
GE2270 factor A A solution of Burgess reagent (3.5 mmol) in dry $CH_2Cl_2$ (5 ml) is added dropwise under an argon atmosphere to a well stirred solution of compound GE I (1 mmol) in dry $CH_2Cl_2$ (15 ml), dry THF (20 ml) and TEA (2.25 ml) at room temperature. After 16 h more Burgess reagent (1 mmol) is added in small portions and stirring is continued at room temperature for further 24 h. The reaction mixture is then evaporated to dryness under reduced pressure and the crude solid is purified by flash chromatography on silica gel 60 (400–230 mesh) using $CH_2Cl_2$/MeOH 95:5 as eluant. The title compound is obtained as a white powder.

Preparation 6: compound GE III

4'-de[4-[[2-(aminocarbonyl)-1-pyrrolidinyl]
carbonyl]-4,5-dihydro-2-oxazolyl]-4'-
(ethoxyiminomethyl)
GE2270 factor A Compound GE II (1 mmol) is dissolved in absolute ethanol (80 ml) and $CHCl_3$ (8 ml). The solution is cooled to 0° C. and dry HCl is bubbled through it for 6 h. The reaction mixture is then allowed to stand overnight at 4° C. and the solvent is evaporated under reduced pressure to a small volume. The concentrated solution is then carefully poured in an aqueous saturated solution of $Na_2CO_3$ and the resulting precipitate is centrifuged, washed twice with water and then redissolved in chloroform containing the minimum amount of ethanol to help solubilizing the product. The resulting solution is then transferred into a separatory funnel to remove the aqueous layer. The organic phase is dried over $Na_2SO_4$ and the solvent evaporated under reduced pressure to yield a white solid which is triturated with ether and filtered. The title compound is obtained as a white powder.

Preparation 7: compound GE IV

9'-de[[2-(aminocarbonyl)-1-pyrrolidinyl]carbonyl]-
9'-(methoxycarbonyl)
GE2270 factor A To a solution of compound GE III (1 mmol) in a mixture of absolute ethanol (35 ml) and $CH_2Cl_2$ (3.5 ml), L-serine methyl ester hydrochloride (1.5 mmol) is added with stirring at room temperature under an argon atmosphere. After 4 days the solvent is evaporated under plates using $CH_2Cl_2$/MeOH 95:5 as eluant. The title compound is obtained as a white powder.

Preparation 8: compound GE V

4'-(R,S)-carboxy-4'-de[[2-(aminocarbonyl)-1-
pyrrolidinyl]-carbonyl]
GE2270 factor A To a solution of compound GE IV (1 mmol) in dioxane (35 ml), 1N NaOH (2 mmol) is added at room temperature with stirring. After 15 min ethyl ether is added to precipitate the title compound which is collected by filtration. The sodium salt of title compound is obtained as white powder.

Preparation of the Amines Starting Materials

Preparation 9: amine for compound 13

Trans-4-hydroxy-L-proline (Aldrich) (30.00 g, 228.7 mmol) is dissolved in a solution of HCl in MeOH 12.9% w/w (250 ml) and the resulting solution is stirred for 48 hours at room temperature. After concentration of the solvent the residue is taken up in ethyl acetate (500 ml) and triethylamine (38.2 ml, 274.4 mmol) and the suspension is stirred at room temperature for 30 min. Inorganic salts are removed by filtration, then the solution is dried ($MgSO_4$) and concentrated to give the pure methyl ester as a white solid.

The above prepared methyl ester (7.23 g, 50 mmol)is dissolved in dioxane (30 ml). A solution of di-t-butylpyrocarbonate (12.0 g, 55 mmol) in dioxane (60 ml)is then added dropwise, dimethylaminopyridine (100 mg, 0.8 mmol)is added and the reaction mixture is stirred for 2 hours at room temperature. The solution is concentrated to a small volume and the residue is taken up in ethyl acetate (300 ml) and washed with 1M aqueous citric acid (100 ml) followed by 1M aqueous sodium hydrogen carbonate (100 ml) and brine (100 ml). The organic solution is dried (MgSO$_4$) and evaporated to dryness to yield the pure N-Boc-protected methyl ester as an oil.

Mesyl chloride (3.87 ml, 50 mmol) is added to a stirred solution of the above prepared N-Boc-protected methyl ester (9.0 g, 36.7 mmol) in dry pyridine (70 ml) at 0° C. Stirring is continued for 4 hours, pyridine is concentrated in vacuo and the residue is taken up in ethyl acetate (100 ml). The solution is washed with 1M aqueous sodium hydrogen carbonate (50 ml), followed by 1M aqueous citric acid (50 ml) and brine (50 ml). The organic solution is dried (MgSO$_4$) and evaporated to dryness and the residue is crystallized from ethyl acetate/light petroleum ether producing the pure O-mesylated derivative as a white powder.

A solution of the above prepared O-mesylated derivative (7.13 g, 22.04 mmol) and sodium azide (1.63 g, 25 mmol) in DMF (30 ml) is heated at 50° C. for 12 hours. The solvent is removed by distillation, then the residue is taken up in ethyl acetate (70 ml) and water (40 ml). The organic phase is washed with brine (4×50 ml) until neutrality of the aqueous phase, washed with 0.1M aqueous HCl (20 ml) and brine (2×50 ml). The organic phase is dried (MgSO$_4$) and the solvent evaporated to dryness in vacuo to yield the pure N-protected cis-4-azido-L-proline methyl ester as a thick oil.

A stirred solution of the above prepared N-protected cis-4-azido-L-proline methyl ester (4.5 g, 16.7 mmol) in THF (20 ml) is reduced by treatment with diethylazodicarboxylate (4.55ml, 25 mmol) and triphenylphosphine (4.39 g, 16.7 mmol) at room temperature for 16 hours. After concentration of the solution to a small volume, the residue is purified by flash chromatography on silica gel 60 (400–230 mesh) with methylene chloride/methanol 95/5 to give the pure cis-4-amino derivative as an oil.

A solution of the above prepared cis-4-amino derivative (2.1 g, 8.72 mmol) in 11% methanolic ammonia (20 ml) is stirred at room temperature for 60 hours. After concentration in vacuo of the solution to a small volume, the residue is precipitated with ethyl acetate to yield pure N-Boc-cis-4-amino-L-prolinamide as an oil.

Preparation 10: amine for compound 14

A solution of N-Cbz-sarcosine (Novabiochem) (2.0 g, 8.96 mmol), N,N,N'(Aldrich) (1.25 ml, 9.86 mmol) and triethylamine (1.40 ml, 9.86 mmol) in dry DMF (30 ml) is stirred at room temperature. DPPA (2.2 ml, 9.86 mmol) is added and stirring at room temperature is continued for 2 hours. The reaction mixture is poured into water (500 ml), the pH is adjusted to 11 by addition of 1N NaOH and the aqueous phase is extracted with ethyl ether (3×200 ml). The organic phase is dried (MgSO$_4$) and concentrated to dryness. The crude product is purified by flash chromatography on silica gel 60 (400–230 mesh) with methylene chloride/methanol 8/2 to produce pure N,N,N'-trimethylethylenediamine N-Cbz-sarcosinamide as an oil.

A suspension of the above prepared N,N,N'-trimethylethylenediamine N-Cbz-sarcosinamide (2.0 g, 6.51 mmol) and 10% palladium on charcoal (200 mg) in 35 methanol (40 ml) is hydrogenated at room temperature and under atmospheric pressure for 1 hour. The catalyst is then removed by filtration and concentration of the solvent produced the pure unprotected N,N,N'-trimethylethylenediamine sarcosinamide as an oil.

Preparation 11: amine for compound 15

A solution of N-Boc-L-alanine N-hydroxy-succinimide ester (Novabiochem) (2.0 g, 7 mmol) and N,N,N'-trimethylethylenediamine (Aldrich) (1.0 ml, 7.7 mmol) in dry DMF (30 ml) is stirred at room temperature overnight and then poured into water (600 ml), the pH is adjusted to 9 with sodium carbonate and the aqueous phase is extracted with ethyl ether (2×400ml). The organic phase is dried (MgSO$_4$) and the solvent is evaporated in vacuo to yield N,N,N'-trimethyl-ethylenediamine N-Boc-L-alaninamide as a colourless oil.

The above prepared N,N,N'-trimethylethylenediamine N-Boc-L-alaninamide (1.7 g, 6.23mmol) is dissolved at 0° C. in anhydrous TFA (10 ml), then stirred for 5 minutes. After concentration of the solvent at low temperature in vacuo and various washings of the oily product with ethyl ether, the crude trifluoroacetate salt is dissolved into water (10 ml), the pH of the aqueous solution is adjusted to 11 with 1N NaOH and then the product is extracted with CH$_2$Cl$_2$ (2×20 ml). The organic phase is dried (MgSO$_4$) and concentrated to dryness in vacuo to give pure N,N,N'-trimethylethylenediamine L-alaninamide trifluoroacetic salt a gummy oil.

Preparation 12: amine for compound 16

A solution of N,N,N'-trimethylethylenediaminesarcosinamide (see preparation 10) (750 mg, 4.33 mmol) in dry THF (15 ml) is stirred under argon at room temperature. Lithium aluminum hydride (495 mg, 13 mmol) is added in one portion, the temperature is brought to reflux and reflux is continued for additional 6 hours. After cooling to 0° C. ethyl acetate (1.5 ml) and 2.5M NaOH (6 ml, 1.2 equivalents) are carefully added followed by solid MgSO$_4$. The suspension is stirred at room temperature for 15 minutes and then filtered. After concentration of the solvent pure N-(2-dimethylaminoethyl)-N-(2-methylaminoethyl)-methylamine is obtained as an oil.

Preparation 13: amine for compound 17

1-Benzylpiperazine (Aldrich) (9 ml, 50 mmol) and potassium carbonate (14 g, 0.1 mole) are added at room temperature to a stirred solution of 3-dimethylaminopropyl chloride hydrochloride (Aldrich) (15.8 g, 0.1 mol) in absolute ethanol (300 ml). The reaction mixture is refluxed for 6 hours, the solvent is evaporated in vacuo and water (300 ml) is added to the resulting oil. After extraction with CH$_2$Cl$_2$ (200 ml), the organic phase is washed with water (200 ml), dried (MgSO$_4$) and the solvent is evaporated in vacuo to yield the 1-benzyl-4-substituted piperazine as an oil.

A suspension of the above prepared 1-benzyl-4-substituted piperazine (9.0 g, 35 mmol) and 10% palladium on charcoal (3 g) in 95% ethanol (300 ml) is hydrogenated at room temperature and under atmospheric pressure for 6 hours. The catalyst is filtered off and the solution is concentrated to dryness under reduced pressure to yield the debenzylated product as an oil.

Preparation 14: amine for compound 18

The reaction is carried out as reported in preparation 10 by condensing N-Cbz-sarcosine (Novabiochem) (2.0 g, 8.96 mmol) with 1-methylpiperazine (Aldrich) (986 mg, 9.86 mmol) and then removing the Cbz-protecting group to yield the expected compound (1.05 g, 68% overall yield) as an oil that is then reduced with lithium aluminum hydride as described in preparation 12 to yield the expected triamine as an oil.

Preparation 15: amine for compound 19

The reaction is carried out as reported in preparation 10 by condensing N-Cbz-sarcosine (Novabiochem) (2.0 g, 8.96 mmol) with N-(2-hydroxy-ethyl)piperazine (Aldrich) (1.28 g, 9.86 mmol) and then removing the Cbz-protecting group to yield the expected compound as an oil that is then reduced with lithium aluminium hydride as described in preparation 12 to yield the expected triaminealcohol as an oil.

Preparation 16: amine for compound 20

1-(4-morpholinocarbonylmethyl)-piperazine (Acros Chimica) (2.13 g, 10 mmol) is reduced as reported in preparation 12 to yield the expected triamine as an oil.

Preparation 17: amine for compound 21

To a solution of (S)-(-)-2-pyrrolidone-5-carboxylic acid (Aldrich) (500 mg, 3.87 mmol), N,N,N'-trimethylethylenediamine (Aldrich) (0.54 ml, 4.26 mmol) and triethylamine (0.60 ml, 4.26 mmol) in dry DMF (5 ml), DPPA (0.95 ml, 4.26 mmol) is added under stirring at room temperature. Stirring is continued for 1 hour, then the mixture is poured into ethyl ether (100 ml). The solid that precipitated is filtered, washed with additional ethyl ether (20 ml) and allowed to dry in air to yield the expected condensation product as a white solid.

Reduction of the above described compound (560 mg, 2.62 mmol) according to preparation 12 yielded the expected triamine as an oil.

Preparation of the Serinamides Starting Materials

Preparation 18: preparation of serinamides for compounds 4s, 10s, 19s and 21s

A mixture of N-Cbz-L-serine (Novabiochem) (100 g, 0.42 mol) and pentafluorophenol (Aldrich) (84.7 g, 0.46 mol) in anhydrous DMF (250 ml) are cooled with stirring under $N_2$ to −10° C. To this solution, a solution of DCC (95.0 g, 0.46 mol) in anhydrous DMF (125 ml) is added over 30 min while keeping the reaction temperature at −10° C. The reaction mixture is stirred at −10° to −5° C. for an additional 30 min and then at room temperature for 3 hours. The reaction mixture is poured into water (3.76 l). After stirring for 15 min, the solid that precipitated out is filtered, washed over the filter with water (3×500 ml) and air dried at room temperature. The solid is then taken up in EtOAc (1 l) and the residual solid (mainly dicyclohexylurea) is filtered off and washed with more EtOAc (3×150 ml). The combined EtOAc solutions are evaporated to dryness under reduced pressure. The residual solid is dissolved in hot $CH_2Cl_2$ (3.2 l). The hot solution is gravity filtered and the solvent is boiled off until solid began to crystallize. The solid which crystallized is filtered and air dried to ambient temperature to give N-Cbz-L-serine pentafluorophenyl ester as a white solid.

Solid N-Cbz-L-serine pentafluorophenyl ester (12.16 g, 0.03 mol) is added over 10 min under $N_2$ atmosphere to a stirred solution of the selected amine (0.03 mol) in $CH_2Cl_2$ (50 ml) at room temperature. At the end of the addition stirring is continued for an additional 1 hour at room temperature and then the reaction mixture is washed with 1N NaOH (3×20 ml). The organic phase is dried (MgSO4) and then evaporated to dryness under reduced pressure to yield the expected N-Cbz-L- serinamides as glassy oils which could be crystallized from $Et_2O$.

Deprotection of the Cbz-protecting group is carried out just before usage of the serinamide.

A suspension of the above prepared N-Cbz-L-serinamide (5.0 g) and 10% palladium on charcoal (500 mg) in methanol (100 ml) is hydrogenated at room temperature and atmospheric pressure in the presence of aqueous 1N HCl for 1 hour. The catalyst is filtered off, washed over the filter with methanol (2×100 ml) and the solvent evaporated to dryness under reduced pressure. Trituration of the waxy solid with $Et_2O$ yielded the expected serinamide hydrochloric salt (80–100%) as white powders.

We claim:

1. Basic amide compounds of GE 2270 and GE 2270-like antibiotics of formula I

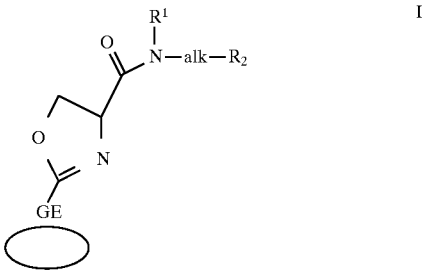

wherein:

$R^1$ represents hydrogen, $(C_1-C_4)$ alkyl or di$(C_1-C_4)$ alkylamino$(C_1-C_4)$alkylene;

alk represents $(C_1-C_4)$alkylene or $(C_1-C_5)$alkylene-carbonyl;

$R^2$ represents aminocarbonyl, mono or di$(C_1-C_4)$ alkylaminocarbonyl, or a $NR^3R^4$ group wherein $R^3$ represents $(C_1-C_4)$alkyl, hydroxy$(C_1-C_4)$alkylene, or di$(C_1-C_4)$alkylamino-$(C_1-C_4)$alkylene, and $R^4$ represents $(C_1-C_4)$alkyl, di$(C_1-C_4)$alkylamino-$(C_1-C_4)$alkylene or hydroxy$(C_1-C_4)$alkylene, or a five or six membered heterocycle ring having one or two nitrogen atoms, or one nitrogen atom and one oxygen atom, with the remaining atoms of the heterocycle ring being carbon atoms, wherein any nitrogen atom or any carbon atom may be optionally substituted with a group selected from$(C_1-C_4)$alkyl, hydroxy$(C_1-C_4)$alkylene, di$(C_1-C_4)$alkylamino and di$(C_1-C_4)$ alkylamino-$(C_1-C_4)$alkylene;

or $R^1$ and alk-$R^2$ together with the adjacent nitrogen atom form a five or six membered heterocycle ring having one or two nitrogen atoms or having one nitrogen atom and one oxygen atom, with the remaining atoms of the heterocycle ring being carbon atoms, wherein any nitrogen atom or any carbon atom may be optionally substituted with a group selected from $(C_1-C_4)$alkyl, di$(C_1-C_4)$alkylamino, di$(C_1-C_4)$alkylamino$(C_1-C_4)$alkylene, hydroxy$(C_1-C_4)$ alkylene and a alk$_2$-$R^5$ group wherein alk$_2$ is $(C_1-C_4)$alkylene and $R^5$ is a $NR^6R^7$ group wherein $R^6$ represents $(C_1-C_4)$alkyl or di$(C_1-C_4)$alkyl-amino $(C_1-C_4)$alkylene and $R^7$ represents $(C_1-C_4)$alkyl or di$(C_1-C_4)$alkyl-amino $(C_1-C_4)$alkylene or a five or six membered heterocycle ring having one or two nitrogen atoms or one nitrogen atom and one oxygen atom, with the remaining atoms of the heterocycle ring being carbon atoms, wherein any nitrogen atom or any carbon atom may be optionally substituted with a group selected from $(C_1-C_4)$alkyl, hydroxy$(C_1-C_4)$alkylene, di$(C_1-C_4)$alkylamino and di$(C_1-C_4)$alkylamino$(C_1-C_4)$alkylene and the group of formula

represents the antibiotic core portion of the formula

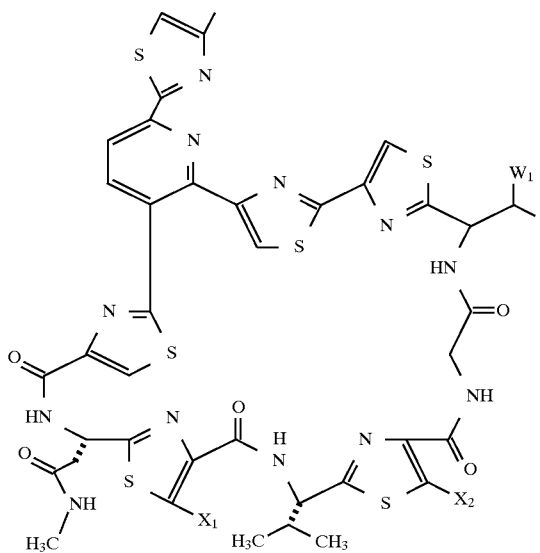

wherein:
$W^1$ represents phenyl
$W^2$ represents hydroxy
or both $W^1$ and $W^2$ represent methyl,
$X^1$ represents hydrogen or methyl,
$X^2$ represents hydrogen, methyl or methoxymethylen,
with the proviso that when both $W^1$ and $W^2$ are methyl, then $X^1$ is methyl and $X^2$ is hydrogen,
or a pharmaceutical acceptable salt thereof.

2. Compound according to claim 1 of formula Ia

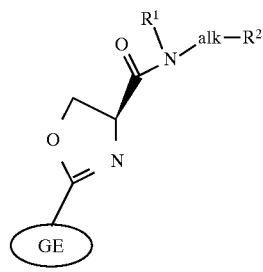

Ia wherein $R^1$, alk, $R^2$ and the group GE are as defined in claim 1.

3. Compound according to claim 1 wherein the group GE is as defined in claim 1 and
$R^1$ represents hydrogen or $(C_1-C_4)$alkyl,
alk represents $(C_1-C_4)$alkylene, $(C_2-C_5)$alkylenecarbonyl,
$R^2$ represents aminocarbonyl or a $NR^3R^4$ group wherein
$R^3$ represents $(C_1-C_4)$alkyl and
$R^4$ represents $(C_1-C_4)$alkyl or di$(C_1-C_4)$alkylamino-$(C_1-C_4)$alkylene,
or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_4)$alkyl and hydroxy$(C_1-C_4)$alkylene;
or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_4)$alkyl, di$(C_1-C_4)$alkylamino, di$(C_1-C_4)$alkylamino$(C_1-C_4)$alkylene and a alk$_2$-$R^5$ group wherein
alk$_2$ is $(C_1-C_2)$alkylene and
$R^5$ is a $NR^6R^7$ group wherein
$R^6$ represents $(C_1-C_4)$alkyl and
$R^7$ represents $(C_1-C_4)$alkyl or di$(C_1-C_4)$alkyl-amino$(C_1-C_4)$alkylene or a five or six membered heterocycle ring having one or two nitrogen atoms or one nitrogen atom and one oxygen atom, with the remaining atoms of the heterocycle ring being carbon atoms.

4. Compound according to claim 1 wherein the group GE is as defined in claim 1 and
$R^1$ represents hydrogen or $(C_1-C_2)$alkyl,
alk represents $(C_1-C_3)$alkylene, $(C_2-C_3)$alkylenecarbonyl,
$R^2$ represents aminocarbonyl or a $NR^3R^4$ group wherein
$R^3$ represents $(C_1-C_3)$alkyl and
$R^4$ represents $(C_1-C_3)$alkyl or di$(C_1-C_2)$alkylamino-$(C_1-C_2)$alkylene,
or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl and hydroxy$(C_1-C_2)$alkylene;
or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl, di$(C_1-C_2)$alkylamino, di$(C_1-C_2)$alkylamino-$(C_1-C_2)$alkylene and a alk$_2$-$R^5$ group wherein
alk$_2$ is $(C_1-C_2)$alkylene and
$R^5$ is a $NR^6R^7$ group wherein
$R^6$ represents $(C_1-C_2)$alkyl and
$R^7$ represents $(C_1-C_2)$alkyl or di$(C_1-C_2)$alkyl-amino$(C_1-C_2)$alkylene
or a five or six membered heterocycle ring having one or two nitrogen atoms or one nitrogen atom and one oxygen atom, with the remaining atoms of the heterocycle ring being carbon atoms.

5. Compound according to claim 1 wherein the group GE is such that $W^1$ is phenyl, $W^2$ is hydroxy, $X^1$ is methyl, $X^2$ is methoxymethylene and
$R^1$ represents hydrogen or $(C_1-C_2)$ alkyl,
alk represents $(C_1-C_3)$alkylene,
$R^2$ represents a $NR^3R^4$ group wherein
$R^3$ represents $(C_1-C_3)$alkyl and
$R^4$ represents $(C_1-C_3)$alkyl or di$(C_1-C_2)$alkylamino-$(C_1-C_2)$alkylene,
or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl or hydroxy$(C_1-C_2)$alkylene;
or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl, di$(C_1-C_2)$alkylamino, di$(C_1-C_2)$alkylamino$(C_1-C_2)$alkylene and a alk$_2$-R$^5$ group wherein alk$_2$ is $(C_1-C_2)$alkylene and
R$^5$ is a NR$^6$R$^7$ group wherein
R$^6$ represents $(C_1-C_2)$alkyl and
R$^7$ represents $(C_1-C_2)$alkyl or di$(C_1-C_2)$alkyl-amino$(C_1-C_2)$alkylene or a five or six membered heterocycle ring having one or two nitrogen atoms or one nitrogen atom and one oxygen atom, with the remaining atoms of the heterocycle ring being carbon atoms.

6. Process for preparing a compound of claim 1 which comprises:
a) reacting a compound of formula III

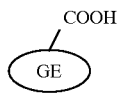

wherein the group GE is as defined in formula I, with a serinamide, or an acid addition salt thereof, of formula IV:

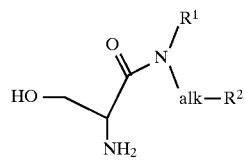

wherein R$^1$, alk and R$^2$ are as in claim 1, in an inert aprotic organic solvent in the presence of a condensing agent;
b) cyclizing the serine moiety of the obtained compound of formula IIIa

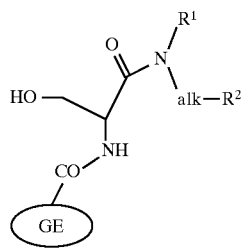

with a suitable cyclizing reactant, in order to obtain the desired compound of formula I.

7. Process for preparing a compound of claim 1 which comprises reacting a compound of formula V

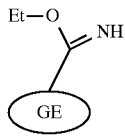

wherein the group GE is as defined in claim 1, with a serinamide, or an acid addition salt thereof, of formula IV:

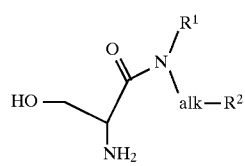

wherein R$^1$, alk and R$^2$ are as in claim 1, in a protic organic solvent.

8. Process for preparing a compound of claim 1 which comprises reacting a compound of formula VI

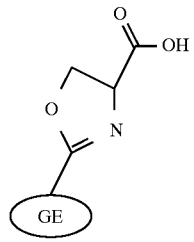

or a base addition salt thereof, wherein the group GE is as defined in formula I, with an amine, or an acid addition salt thereof, of formula IVa:

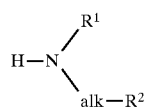

wherein R$^1$, alk, and R$^2$ are as defined in formula I, in the presence of an inert organic solvent and of a condensing agent.

9. Compound of formula

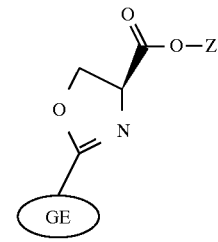

wherein Z represents $(C_1-C_4)$alkyl and GE is as defined in claim 1.

10. Compound according to claim 2 wherein the group GE is as defined in claim 1 and
R$^1$ represents hydrogen or $(C_1-C_4)$ alkyl,
alk represents $(C_1-C_4)$alkylene, $(C_2-C_5)$alkylene-carbonyl,
R$^2$ represents aminocarbonyl or a NR$^3$R$^4$ group wherein
R$^3$ represents $(C_1-C_4)$alkyl and
R$^4$ represents $(C_1-C_4)$alkyl or di$(C_1-C_4)$alkylamino-$(C_1-C_4)$alkylene, or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_4)$alkyl and hydroxy$(C_1-C_4)$alkylene;

or R$^1$ and alk-R$^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_4)$alkyl, di$(C_1-C_4)$alkylamino, di$(C_1-C_4)$alkylamino$(C_1-C_4)$alkylene and a alk$_2$-R$^5$ group wherein alk$_2$ is $(C_1-C_2)$alkylene and
R$^5$ is a NR$^6$R$^7$ group wherein
R$^6$ represents $(C_1-C_4)$alkyl and
R$^7$ represents $(C_1-C_4)$alkyl or di$(C_1-C_4)$alkyl-amino$(C_1-C_4)$alkylene or a five or six membered heterocycle ring having one or two nitrogen atoms or one nitrogen atom and one oxygen atom, with the remaining atoms of the heterocycle ring being carbon atoms.

11. Compound according to claim 2 wherein the group GE is as defined in claim 1 and $R^1$ represents hydrogen or $(C_1-C_2)$alkyl, alk represents $(C_1-C_3)$alkylene, $(C_2-C_3)$alkylene-carbonyl, $R^2$ represents aminocarbonyl or a $NR^3R^4$ group wherein
  $R^3$ represents $(C_1-C_3)$alkyl and
  $R^4$ represents $(C_1-C_3)$alkyl or di$(C_1-C_2)$alkylamino-$(C_1-C_2)$alkylene,
  or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl and hydroxy$(C_1-C_2)$alkylene;

or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl, di$(C_1-C_2)$alkylamino, di$(C_1-C_2)$alkylamino-$(C_1-C_2)$alkylene and a alk$_2$-$R^5$ group wherein alk$_2$ is $(C_1-C_2)$alkylene and $R^5$ is a $NR^6R^7$ group wherein
  $R^6$ represents $(C_1-C_2)$alkyl and
  $R^7$ represents $(C_1-C_2)$alkyl or di$(C_1-C_2)$alkyl-amino $(C_1-C_2)$alkylene
  or a five or six membered heterocycle ring having one or two nitrogen atoms or one nitrogen atom and one oxygen atom, with the remaining atoms of the heterocycle ring being carbon atoms.

12. Compound according to claim 2 wherein the group GE is such that $W^1$ is phenyl, $W^2$ is hydroxy, $X^1$ is methyl, $X^2$ is methoxymethylene and $R^1$ represents hydrogen or $(C_1-C_2)$alkyl, alk represents $(C_1-C_3)$alkylene, $R^2$ represents a $NR^3R^4$ group wherein
  $R^3$ represents $(C_1-C_3)$alkyl and
  $R^4$ represents $(C_1-C_3)$alkyl or di$(C_1-C_2)$alkylamino-$(C_1-C_2)$alkylene,
  or a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl and hydroxy$(C_1-C_2)$alkylene;

or $R^1$ and alk-$R^2$ together with the adjacent nitrogen atom form a five or six membered heterocycle ring having one or two nitrogen atoms, with the remaining atoms of the heterocycle ring being carbon atoms, wherein any nitrogen atom or any carbon atom may be optionally substituted with a group selected from $(C_1-C_2)$alkyl, di$(C_1-C_2)$alkylamino, di$(C_1-C_2)$alkylamino-$(C_1-C_2)$alkylene and a alk$_2$-$R^5$ group wherein alk$_2$ is $(C_1-C_2)$alkylene and $R^5$ is a $NR^6R^7$ group wherein
  $R^6$ represents $(C_1-C_2)$alkyl and
  $R^7$ represents $(C_1-C_2)$alkyl or di$(C_1-C_2)$alkyl-amino $(C_1-C_2)$alkylene
  or a five or six membered heterocycle ring having one or two nitrogen atoms or one nitrogen atom and one oxygen atom, with the remaining atoms of the heterocycle ring being carbon atoms.

13. Pharmaceutical composition containing a compound of claim 1 in admixture with a pharmaceutically acceptable carrier.

14. Pharmaceutical composition containing a compound of claim 2 in admixture with a pharmaceutically acceptable carrier.

15. Pharmaceutical composition containing a compound of claim 3 in admixture with a pharmaceutically acceptable carrier.

16. Pharmaceutical composition containing a compound of claim 4 in admixture with a pharmaceutically acceptable carrier.

17. Pharmaceutical composition containing a compound of claim 5 in admixture with a pharmaceutically acceptable carrier.

18. Method for the treatment of bacterial infections comprising administering an effective amount of a compound of claim 1 to a patient in need thereof.

19. Method for the treatment of bacterial infections comprising administering an effective amount of a compound of claim 2 to a patient in need thereof.

20. Method for the treatment of bacterial infections comprising administering an effective amount of a compound of claim 3 to a patient in need thereof.

21. Method for the treatment of bacterial infections comprising administering an effective amount of a compound of claim 4 to a patient in need thereof.

22. Method for the treatment of bacterial infections comprising administering an effective amount of a compound of claim 5 to a patient in need thereof.

23. A compound according to claim 1 which is

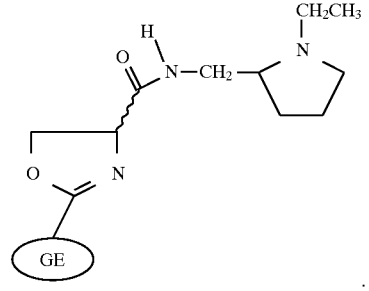

24. A compound according to claim 1 which is
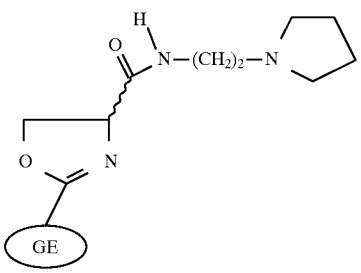
25. A compound according to claim 1 which is
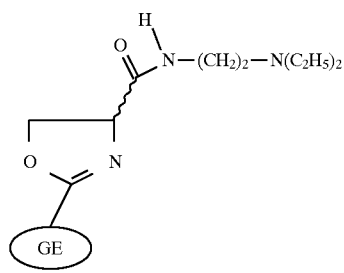
26. A compound according to claim 1 which is
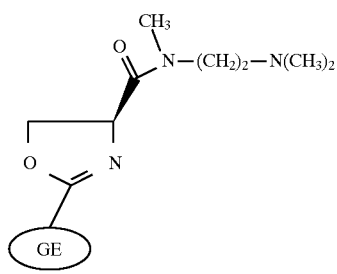
27. A compound according to claim 1 which is
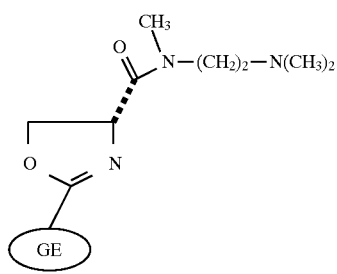
28. A compound according to claim 1 which is
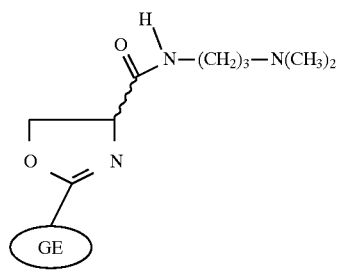
29. A compound according to claim 1 which is
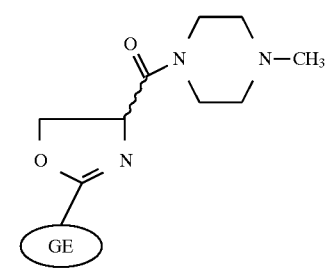
30. A compound according to claim 1 which is
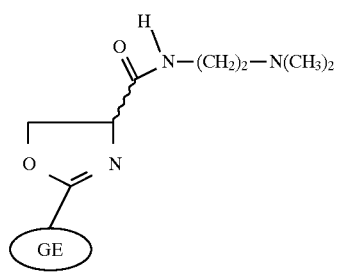
31. A compound according to claim 1 which is
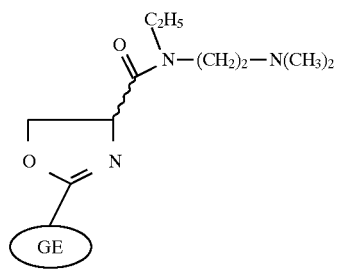

32. A compound according to claim 1 which is
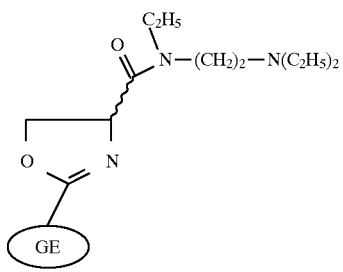
33. A compound according to claim 1 which is
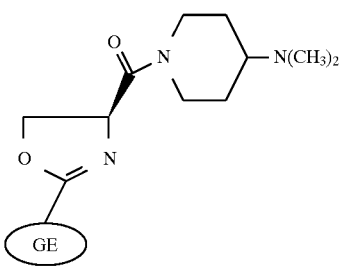
34. A compound according to claim 1 which is
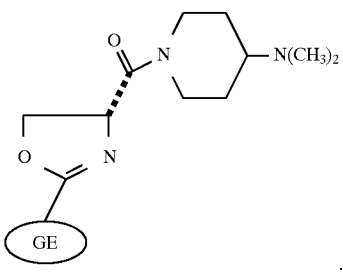
35. A compound according to claim 1 which is
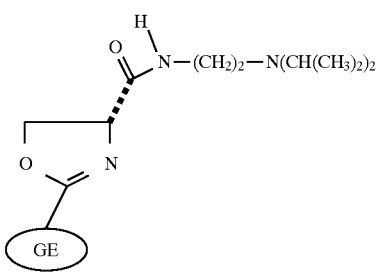
36. A compound according to claim 1 which is
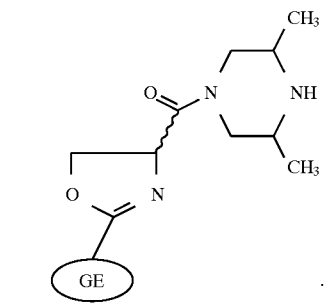
37. A compound according to claim 1 which is
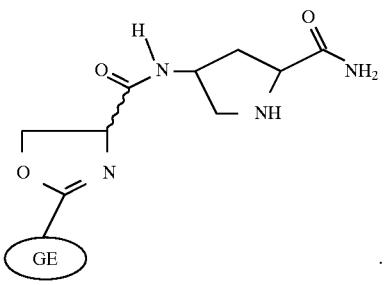
38. A compound according to claim 1 which is
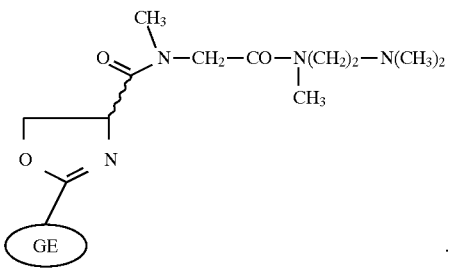
39. A compound according to claim 1 which is
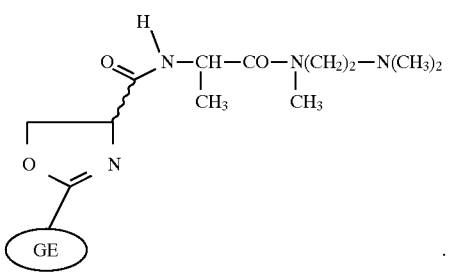

40. A compound according to claim 1 which is
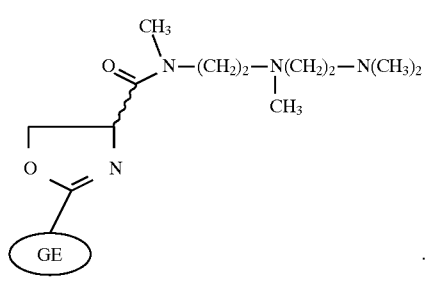
41. A compound according to claim 1 which is
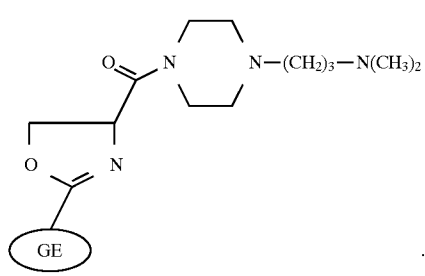
42. A compound according to claim 1 which is
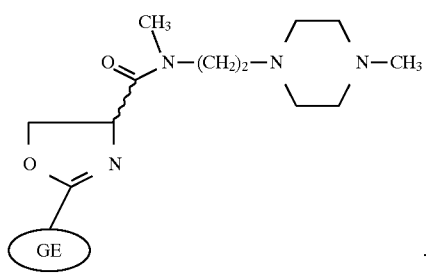
43. A compound according to claim 1 which is
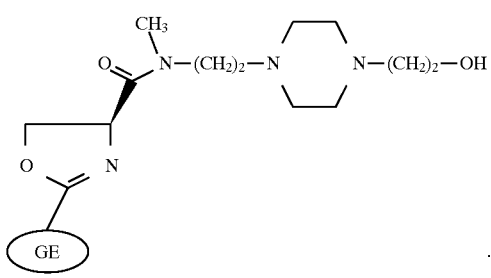
44. A compound according to claim 1 which is
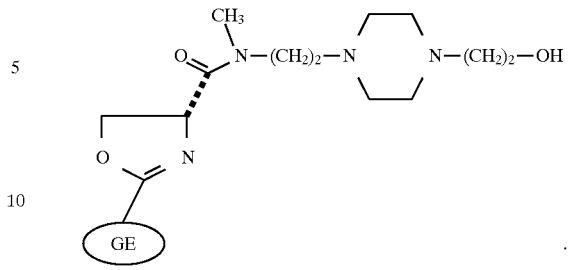
45. A compound according to claim 1 which is
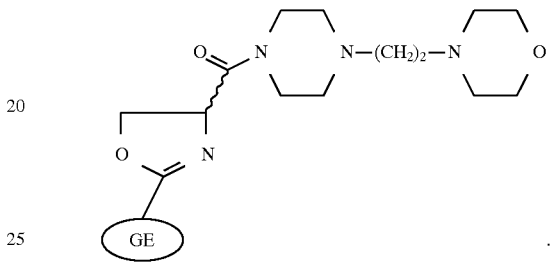
46. A compound according to claim 1 which is
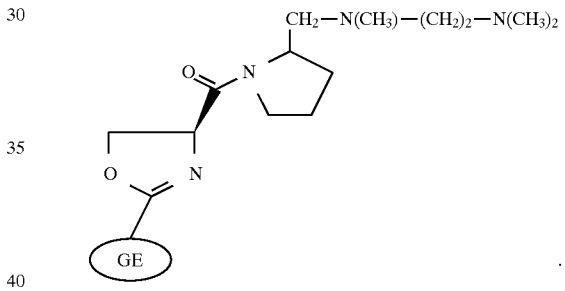
47. A compound according to claim 1 which is
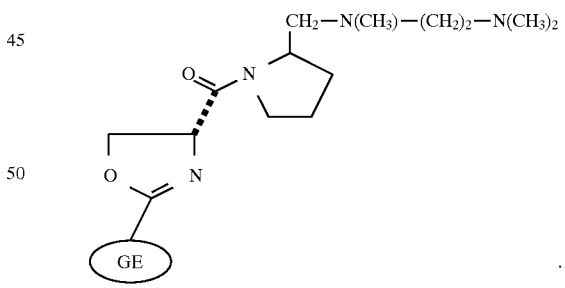
* * * * *